US007803376B2

(12) United States Patent
Velardi et al.

(10) Patent No.: US 7,803,376 B2
(45) Date of Patent: Sep. 28, 2010

(54) METHODS AND COMPOSITIONS FOR INCREASING THE EFFICIENCY OF THERAPEUTIC ANTIBODIES USING NK CELL POTENTIATING COMPOUNDS

(75) Inventors: Andrea Velardi, Perugia (IT); Francois Romagne, La Ciotat (FR)

(73) Assignee: Innate Pharma S.A., Marseilles (FR)

( * ) Notice: Subject to any disclaimer, the term of this patent is extended or adjusted under 35 U.S.C. 154(b) by 1131 days.

(21) Appl. No.: 10/897,624

(22) Filed: Jul. 23, 2004

(65) Prior Publication Data
US 2005/0037002 A1 Feb. 17, 2005

Related U.S. Application Data

(60) Provisional application No. 60/489,489, filed on Jul. 24, 2003.

(51) Int. Cl.
A61K 39/395 (2006.01)
(52) U.S. Cl. ............... 424/144.1; 424/130.1; 424/143.1
(58) Field of Classification Search ....................... None
See application file for complete search history.

(56) References Cited

U.S. PATENT DOCUMENTS

| 6,455,043 B1* | 9/2002 | Grillo-Lopez ............ 424/155.1 |
| 2003/0026804 A1 | 2/2003 | Grillo-Lopez |
| 2003/0095965 A1 | 5/2003 | Van Beneden et al. |

FOREIGN PATENT DOCUMENTS

| EP | 1023906 A1 | 8/2000 |
| WO | WO 02/34290 A3 | 5/2002 |

OTHER PUBLICATIONS

Faure et al. ,Journal of Immonology, 2002, 168:6208-6214.*
Winter et al.,Journal of Immunology, 1998, 161:571-577.*
Harjunpaa et al. Scan, J. Immunology, 2000, vol. 51, p. 634-641.*
Campbell, Monoclonal Antibody Technology, 1984, Elsevier, p. 1-32.*
Gavilondo, Biotechnology, 2000, vol. 29 (1): 128-145.*
Trinchieri, J. Exp. Med, 1994, vol. 180, p. 417-421.*
Lanier et al. Immunol. Reviews, 1997, vol. 155, p. 145-154.*
Campbell, P. et al. "Monoclonal Antibody Therapy for Lymphoma" *Blood Reviews*, 2003, pp. 143-152, vol. 17.
Farag, S. S. et al. "New Directions in Natural Killer Cell-Based Immunotherapy of Human Cancer" *Expert Opin. Biol. Ther.*, 2003, pp. 237-250, vol. 3, No. 2.
Koh, C. Y. et al. "Augmentation of Antitumor Effects by NK Cell Inhibitory Receptor Blockade in Vitro and in Vivo" *Blood*, May 15, 2001, pp. 3132-3137, vol. 97, No. 10.
Moretta, A. et al. "Novel Surface Molecules Involved in Human NK Cell Activation and Triggering of the Lytic Machinery" *Int. J. Cancer*, 1992, pp. 6-10, vol. 7, Supplement.
Sivori, S. et al. "P46, A Novel Natural Killer Cell-Specific Surface Molecule that Mediates Cell Activation" *J. Exp. Med.*, Oct. 6, 1997, pp. 1129-1136, vol. 186, No. 7.
Sondel, P. M. et al. "Combination Therapy with Interleukin-2 and Antitumor Monoclonal Antibodies" *Cancer Journal from Scientific American*, 1997, pp. S121-S127, vol. 3, Supplement 1.
Biassoni, R. et al. (1993) "Human CD3-CD16+ natural killer cells express the hGATA-3 T cell transcription factor and an unrearranged 2.3-kb TcR δ transcript" *Eur. J. Immunol.* 23:1083-1087.
Karre, K. et al. (1986) "Selective rejection of H-2-deficient lymphoma variants suggests alternative immune defence strategy" *Nature* 319:675-678.
Lanier, L.L. (1998) "NK cell receptors" *Annu. Rev. Immunol.* 16:359-393.
Moretta, A. et al. (1990) "Identification of four subsets of human CD3-CD16+ natural killer (NK) cells by expression of clonally distributed functional surface molecules: Correlation between subset assignment of NK clones and ability to mediate specific alloantigen recogniction" *J. Exp. Med.* 172:1589-1598.
Moretta A. et al. (1993) "P58 molecules as putative receptors for major histocompatibility complex (MHC) class I molecules in human natural killer (NK) cells. Anti-p58 antibodies reconstitute lysis of MHC class I-protected cells in NK clones displaying different specificities" *J. Exp. Med.* 178:597-604.
Moretta, A. and L. Moretta (1997) "HLA class I specific inhibitory receptors" *Current Opin. Immunol.* 9:694-701.
Ohlen, C. et al. (1989) "Prevention of allogeneic bone marrow graft rejection by H-2 transgene in donor mice" *Science* 246(4930):666-668.
Pende, D. et al. (1999) "Identification and molecular characterization of NKp30, a novel triggering receptor involved in natural cytotoxicity mediated by human natural killer cells" *J. Exp. Med.* 190(10):1505-1516.
Ruggeri, L. et al. (2002) "Effectiveness of donor natural killer cell alloreactivity in mismatched hematopoietic transplants" *Science* 295:2097-2100.
Saulquin, X. et al. (2003) "Crystal structure of the human natural killer cell activating receptor KIR2DS2 (CD158j)" *J. Exp. Med.* 197(7):933-938.
Valiante, N. et al. (1997) "Killer cell receptors: Keeping pace with MHC class I evolution" *Immunological Rev.* 1997 155:155-164.
Wagtmann, N. et al. (1995) "Molecular clones of the p58 NK cell receptor reveal immunoglobulin-related molecules with diversity in both the extra- and intracellular domains" *Immunity* 2:439-449.
Ward, E.S. et al. (1989) "Binding activities of a repertoire of single immunoglobulin variable domains secreted from *Escherichia coli*" *Nature* 341:544-546.

* cited by examiner

*Primary Examiner*—Michael Szperka
*Assistant Examiner*—Yunsoo Kim
(74) *Attorney, Agent, or Firm*—Saliwanchik, Lloyd & Saliwanchik

(57) ABSTRACT

The present invention relates, generally, to methods and compositions for increasing the efficiency of therapeutic antibodies. Their efficiency is enhanced through the increase of the ADCC mechanism. More particularly, the invention relates to the use of a therapeutic antibody in combination with compounds that block an inhibitory receptor or stimulate an activating receptor of an NK cell in order to enhance the efficiency of the treatment with therapeutic antibodies in human subjects.

24 Claims, 4 Drawing Sheets

US 7,803,376 B2

SEQUENCE LISTING

```
<160> NUMBER OF SEQ ID NOS: 2

<210> SEQ ID NO 1
<211> LENGTH: 42
<212> TYPE: DNA
<213> ORGANISM: Artificial Sequence
<220> FEATURE:
<223> OTHER INFORMATION: Primer - Sense - 5' to 3'

<400> SEQUENCE: 1
ggaattccag gaggaattta aaatgcatga gggagtccac ag                           42

<210> SEQ ID NO 2
<211> LENGTH: 36
```

-continued

```
<212> TYPE: DNA
<213> ORGANISM: Artificial Sequence
<220> FEATURE:
<223> OTHER INFORMATION: Primer - Antisense - 5' to 3'

<400> SEQUENCE: 2
cccaagcttg ggttatgtga cagaaacaag cagtgg                              36
```

METHODS AND COMPOSITIONS FOR INCREASING THE EFFICIENCY OF THERAPEUTIC ANTIBODIES USING NK CELL POTENTIATING COMPOUNDS

CROSS-REFERENCE TO RELATED APPLICATIONS

This application claims the benefit of U.S. Provisional Application Ser. No. 60/489,489, filed on Jul. 24, 2003, which is hereby incorporated by reference in its entirety, including all figures, tables, amino acid sequences and polynucleotide sequences.

FIELD OF THE INVENTION

The present invention relates, generally, to methods and compositions for increasing the efficiency of therapeutic antibodies. More particularly, the invention relates to the use of a therapeutic antibody in combination with a compound that blocks an inhibitory receptor or stimulates an activating receptor of natural killer cells, thereby allowing a potentiation of natural killer cell cytotoxicity in mammalian subjects in order to enhance the efficiency of the treatment in human subjects, particularly through an increase of the ADCC mechanism.

BACKGROUND OF THE INVENTION

Various therapeutic strategies in human beings are based on the use of therapeutic antibodies. These include, for instance, the use of therapeutic antibodies developed to deplete target cells, particularly diseased cells such as virally-infected cells, tumor cells or other pathogenic cells. Such antibodies are typically monoclonal antibodies, of IgG species, typically with human IgG1 or IgG3 Fc portions. These antibodies can be native or recombinant antibodies, and are often "humanized" mice antibodies (i.e., comprising functional domains from various species, typically an Fc portion of human or non human primate origin, and with a variable region or complementary determining region (CDR) of mouse origin). Alternatively, the monoclonal antibody can be fully human through immunization in transgenic mice having the human Ig locus, or obtained through cDNA libraries derived from human cells.

A particular example of such therapeutic antibodies is rituximab (Mabthera®, Rituxan®), which is a chimeric anti-CD20 monoclonal antibody made with human γ1 and κ constant regions (therefore with human IgG1 Fc portion) linked to murine variable domains conferring CD20 specificity. In the past few years, rituximab has considerably modified the therapeutical strategy against B lymphoproliferative malignancies, particularly non-Hodgkin's lymphomas (NHL). Other examples of humanized IgG1 antibodies include alemtuzumab (Campath-1H®), which is used in the treatment of B cell malignancies, and trastuzumab (Herceptin®), which is used in the treatment of breast cancer. Additional examples of therapeutic antibodies under development are disclosed in the art.

The mechanism of action of therapeutic antibodies is still a matter of debate. Injection of antibodies leads to depletion of cells bearing the antigen specifically recognized by the antibody. This depletion can be mediated through at least three mechanisms: antibody mediated cellular cytotoxicity (ADCC), complement dependant lysis, and direct antitumor inhibition of tumor growth through signals given via the antigen targeted by the antibody.

While these antibodies represent a novel and efficient approach to human therapy, particularly for the treatment of tumors, they do not always exhibit a strong efficacy. For instance, while rituximab, alone or in combination with chemotherapy, was shown to be effective in the treatment of both low-intermediate and high-grade NHL, 30% to 50% of patients with low grade NHL have no clinical response to rituximab. It has been suggested that the level of CD20 expression on lymphoma cells, the presence of high tumor burden at the time of treatment, or low serum rituximab concentrations may explain the lack of efficacy of rituximab in some patients. Nevertheless, the actual causes of treatment failure remain largely unknown.

Further, the use of therapeutic antibodies can be limited by side effects caused by their administration. For example, side effects such as fever, headaches, nausea, hypotension, wheezing, rashes, infections, and numerous others can appear in patients, potentially limiting the possible amount or frequency with which the antibodies can be administered.

Thus, it would be very interesting to increase the efficacy of therapeutic antibodies, or to be able to achieve therapeutic efficacy using reduced doses of the antibodies that are less likely to produce side effects. The present invention addresses these and other needs.

SUMMARY OF THE INVENTION

The present invention discloses novel approaches to enhance the efficacy of therapeutic antibodies. Without being limited by the following theory, it is believed that the surprising results achieved using the present methods stem from their ability to enhance the ADCC mechanism in vivo, when therapeutic antibodies are injected. Indeed, the present invention provides novel compositions and methods that overcome the current difficulty related to the efficacy of therapeutic antibodies. It is shown in the present invention that NK cells from an individual can have poor therapeutic mAb (monoclonal antibody)-mediated ADCC because of a lack of activation of NK cells, e.g., by an inhibition of inhibitory receptors on NK cells. Preferably, an increase of the ADCC mechanism is achieved by the administration of compounds that block an inhibitory receptor, or stimulate an activating receptor, on natural killer cells, thereby promoting a potentiation of natural killer cell cytotoxicity in mammalian subjects. Preferably the compound is an antibody or a fragment thereof. Said antibodies or other compounds can react with an inhibitory receptor of NK cells, e.g., Killer inhibitory receptor (KIR or NKG2A/C) molecules, or with activating receptors, e.g., NCRs such as NKp30, NKp44, or NKp46, on NK cells, thereby neutralizing the inhibition of the cells and increasing their ADCC activity.

More specifically, the invention discloses methods of treatments of a subject in which a compound, preferably an antibody or a fragment thereof, that blocks an inhibitory receptor or stimulates an activating receptor of an NK cell, is co-administered with the therapeutic antibody to the subject. The inventors demonstrate here that the efficiency of a therapeutic antibody can be greatly enhanced by the co-administration, e.g., co-injection, of such a compound, preferably an antibody or a fragment thereof, that overcomes the inhibition of NK cells, e.g., by blocking the inhibitory receptor or stimulating an activating receptor of an NK cell.

The invention also concerns pharmaceutical compositions comprising a therapeutic antibody and a compound, preferably an antibody or a fragment thereof, that blocks an inhibitory receptor or stimulates an activating receptor of an NK cell. The invention also concerns kits comprising a therapeutic antibody and a compound, preferably an antibody or a fragment thereof, that blocks an inhibitory receptor or stimulates an activating receptor of an NK cell.

The invention also concerns the use of a compound, preferably an antibody or a fragment thereof that blocks the inhibitory receptor or stimulates an activating receptor of an NK cell, for increasing the efficiency of a treatment with a therapeutic antibody, or for increasing ADCC in a subject submitted to a treatment with a therapeutic antibody.

The invention also concerns the use of a compound, preferably an antibody or a fragment thereof, that blocks the inhibitory receptor or stimulates an activating receptor of an NK cell, and of a therapeutic antibody for the preparation of a drug for treating a disease. More particularly, the treatment of the disease requires the depletion of the targeted cells, preferably the diseased cells such as virally-infected cells, tumor cells or other pathogenic cells. Preferably, the disease is a cancer, infectious or immune disease. More preferably, the disease is selected from the group consisting of a cancer, an auto-immune disease, an inflammatory disease, and a viral disease. The disease also concerns a graft rejection, more particularly allograft rejection, and graft versus host disease (GVHD).

The present invention also comprises a method for reducing the dosage of a therapeutic antibody, e.g., an antibody that is bound by an Fcγ receptor, preferably CD16 (FcγRIIIa). For example, co-administration of a therapeutic antibody and a compound that blocks an inhibitory receptor or stimulates an activating receptor on NK cells allows a lower dose of the therapeutic antibody to be used. Such antibodies can be used at a 20%, 30%, 40%, 50%, 60%, 70%, 80%, 90%, or lower dose than the recommended dose in the absence of the compound.

In addition, the invention provides a method for determining a therapeutically-effective, reduced dose of a therapeutic antibody, e.g., an antibody bound by CD16, the method comprising i) co-incubating a first concentration of the therapeutic antibody with target cells and NK cells, and in the absence of a compound that blocks an inhibitory receptor or stimulates an activating receptor on NK cells; ii) co-incubating a second, lower concentration of the therapeutic antibody with target cells, with NK cells, and in the presence of a compound that blocks an inhibitory receptor or stimulates an activating receptor on NK cells; iii) determining if the depletion of target cells observed in step ii) is as great as the depletion observed in step i). If it is observed that step ii) is as efficacious as step i), then the relative concentrations of the compound and the therapeutic antibody can be varied, and depletion observed, in order to identify different conditions that would be suitable for use in a given patient, e.g., maximizing target cell depletion, lowered dose of therapeutic antibody, or lowered dose of the compound, depending on the particular needs of the patient.

In a particular aspect, the present invention provides a method of treatment of a disease in a human subject in need thereof, comprising: a) administering to said subject a compound that blocks an inhibitory receptor or stimulates an activating receptor of an NK cell; and, b) administering to said subject a therapeutic antibody that can be bound by CD16.

In one embodiment, the therapeutic antibody and compound are administered into the subject simultaneously. In another embodiment, the compound is administered to the subject within one week, within 4 days, within 3 days or on the same day (e.g., within about 24 hours) of the administration of the therapeutic antibody. In another embodiment, the disease is a cancer, infectious or immune disease.

In one embodiment, the method further comprising an additional step in which the activity or number of NK cells in the subject is assessed prior or subsequent to the administration of the compound. In another embodiment, the additional step involves i) obtaining NK cells from the subject prior to the administration; ii) incubating the NK cells in the presence of one or more target cells that are recognized by the therapeutic antibody, in the presence or absence of the compound; and iii) assessing the effect of the compound on the ability of the NK cells to deplete the target cells; wherein a detection that the compound enhances the ability of the NK cells to deplete the target cells indicates that the compound is suitable for use in the method, and that the method is suitable for use with the subject.

In another aspect, the present invention provides a pharmaceutical composition comprising a therapeutic antibody, e.g., that can be bound by CD16, a compound that blocks an inhibitory receptor or stimulates an activating receptor of NK cells, and a pharmaceutically acceptable carrier. In another aspect, the present invention provides a kit comprising a therapeutic antibody, e.g., that can be bound by CD16, and one or more compounds that block an inhibitory receptor or stimulate an activating receptor of NK cells.

For any of the above-mentioned methods, compositions, or kits, in one embodiment the therapeutic antibody has a human IgG1 or an IgG3 Fc portion. In another embodiment, the compound is an antibody or a fragment thereof. In another embodiment, the therapeutic antibody is a monoclonal antibody or fragment thereof. In another embodiment, the therapeutic antibody is not conjugated with a radioactive or toxic moiety. In another embodiment, the compound inhibits an inhibitory receptor of an NK cell. In another embodiment, the compound stimulates an activating receptor of an NK cell. In another embodiment, the compound is a human, humanized or chimeric antibody, or a fragment thereof. In one embodiment, the therapeutic antibodies or compounds can be antibody fragments or derivatives such as, inter alia, a Fab fragment, a Fab'2 fragment, a CDR and a ScFv.

In one embodiment, the therapeutic antibody is a human, humanized or chimeric antibody or a fragment thereof. In another embodiment, the therapeutic antibody is rituximab or Campath. In another embodiment, the antibody is rituximab, and said antibody is administered at a dosage of less than 375 mg/m$^2$ per week. In another embodiment, the antibody is Campath, and the antibody is administered at a dosage of less than 90 mg per week.

In one embodiment, the compound binds at least one of NKG2, KIR2DL or KIR3DL human receptors, and inhibits the related NKG2, KIR2DL- or KIR3DL-mediated inhibition of NK cell cytotoxicity. In another embodiment, the compound blocks an inhibitory receptor of an NK cell selected from the group consisting of KIR2DL1, KIR2DL2/3, KIR2DL4, KIR2DL5A, KIR2DL5B, KIR3DL1, KIR3DL2, KIR3DL3, LILRB1, NKG2A, NKG2C NKG2E and LILRB5. In another embodiment, the compound binds a common determinant of KIR2DL human receptors and inhibits KIR2DL-mediated inhibition of NK cell cytotoxicity. In another embodiment, the compound binds a common determinant of KIR2DL 1, KIR2DL2, and KIR2DL3 human receptors and inhibits KIR2DL1-, KIR2DL2-, and KIR2DL3-mediated inhibition of NK cell cytotoxicity. In another embodiment, the compound inhibits the binding of a HLA-C allele molecule having a Lys residue at position 80 to a human KIR2DL1 receptor, and the binding of a HLA-C allele molecule having an Asn residue at position 80 to human KIR2DL2 and KIR2DL3 receptors. In another embodiment, the compound binds to the same epitope as monoclonal antibody DF200 produced by hybridoma DF200. In another embodiment, the compound competes with monoclonal antibody DF200 produced by hybridoma DF200 for binding to a KIR receptor at the surface of a human NK cell. In another embodiment, the compound is monoclonal antibody DF200 produced by hybridoma DF200 or a fragment thereof.

In one embodiment, the compound binds to a receptor selected from the group consisting of NKp30, NKp44, NKp46, and NKG2D. In another embodiment, the compound is derived from or competes with a monoclonal antibody selected from the group consisting of AZ20, A76, Z25, Z231, and BAB281.

In another aspect, the present invention provides a method of selecting a compound for administration in conjunction with a therapeutic antibody, said method comprising: i) providing a test compound that inhibits an inhibitory receptor or stimulates an activating receptor of NK cells; ii) incubating the therapeutic antibody with target cells specifically recognized by the therapeutic antibody in the presence of NK cells and in the presence or absence of the test compound; and iii) assessing the effect of the compound on the ability of the NK cells to deplete the target cells; wherein a detection that the compound enhances the ability of the NK cells to deplete the target cells indicates that the compound is suitable for use in the method.

In one embodiment, the compound enhances the ability of the therapeutic antibody to destroy the target cells by 50%, 60%, 70%, 80%, 90%, 100%, 200%, 300%, 400%, 500%, or more. In another embodiment, the compound is selected from the group consisting of an antibody, an antibody fragment, a monoclonal antibody, a fragment of a monoclonal antibody, a humanized antibody, a chimeric antibody, and a human antibody. In another embodiment, the target cells are cancer cells, virally infected cells, or cells underlying an autoimmune disorder. In another embodiment, the therapeutic antibody is rituximab or CAMPATH.

In another aspect, the present invention provides a method of increasing the efficiency of a treatment involving the administration of a therapeutic antibody that can be bound by CD16 in a subject, said method comprising administering to said subject prior to, simultaneously with, or after the administration of said therapeutic antibody, a therapeutically-effective amount of a compound that blocks an inhibitory receptor or stimulates an activating receptor of an NK cell. In one embodiment, the compound increases the efficiency of the treatment by enhancing ADCC in said subject.

BRIEF DESCRIPTION OF THE DRAWINGS

FIG. 1A: Clone CP11 KIR2DL1+ DF200; FIG. 1B: Clone CP11 KIR2DL1+ANTIKIR2DL1; FIG. 1C: Clone CP502 KIR2DL3+DF200; FIG. 1D: Clone CP502 KIRDL3+ANTIKIR2DL2/3.

DETAILED DESCRIPTION OF THE INVENTION

Figure 1C:
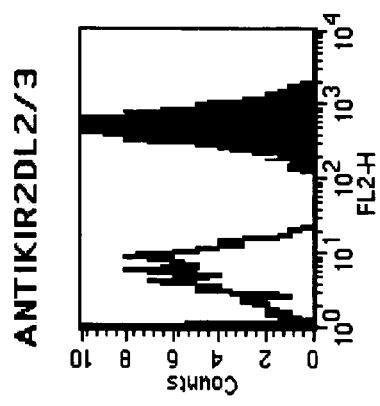
FIGS. 1A-1D: Monoclonal antibody DF200 binds a common determinant of various human KIR2DL receptors. One of the monoclonal antibodies, the DF200 mAb, was found to react with various members of the KIR family, including: KIR2DL1 and KIR2DL2/3. Regarding the staining of NK cells with DF200 mAb, both KIR2DL1+ and KIR2DL2/3+ cells were stained brightly.
Figure 1D:
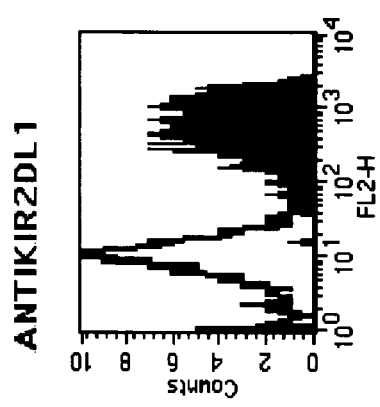
Figure 1A:
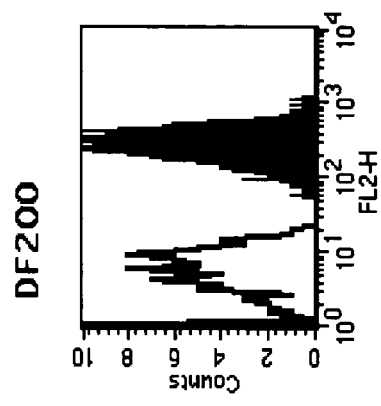
Figure 1B:
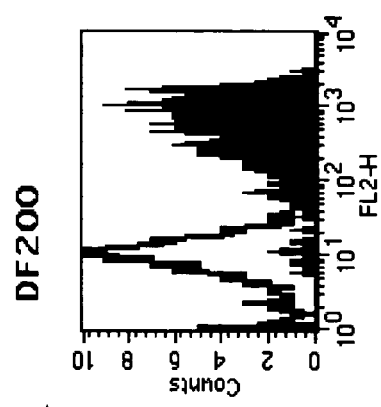

The present invention provides a method for increasing the efficiency of therapeutic antibodies. The invention more specifically discloses that the use of a compound, preferably an antibody or a fragment thereof, that potentiates NK cells, preferably by blocking an inhibitory receptor or activating an activating receptor of an NK cell, can significantly increase the efficiency of therapeutic antibodies. Indeed, the inventors demonstrate that the efficiency of multiple therapeutic antibodies can be greatly enhanced by the co-administration of an antibody directed against an NK cell receptor; e.g., an inhibitory receptor.

Therefore, the invention concerns a method of treatment of a disease in a subject in need thereof comprising:

a) administering to said subject a compound, preferably an antibody or a fragment thereof, that blocks an inhibitory receptor or stimulates an activating receptor of an NK cell; and, b) administering to said subject a therapeutic antibody.

Said therapeutic antibody can be bound by CD16 of NK cells, preferably through its Fc region.

Preferably, said therapeutic antibody has a human IgG1 or an IgG3 Fc portion, particularly a monoclonal antibody or a fragment thereof, further preferably a humanized, human or chimeric antibody or a fragment thereof, for instance rituximab.

It is intended that compounds, preferably antibodies or a fragment thereof, that block the inhibitory receptor of an NK cell can be administered to the subject before, simultaneously with or, after the administration of the therapeutic antibody. The way of administration of the different antibodies depends on their bioavailability and phamacokinetics. Preferably, the therapeutic antibody is administered within a week to the administration of the compounds, preferably antibodies or a fragment thereof, that block the inhibitory receptor of an NK cell, more preferably within the 5 or 2 days period. Preferably, the therapeutic antibody is administered before or simultaneously with the compounds, preferably antibodies or a fragment thereof, that block the inhibitory receptor of an NK cell.

In a further aspect, the invention concerns a method of increasing ADCC in a subject receiving a therapeutic antibody treatment, said method comprising administering to said subject prior to, simultaneously or after the administration of said therapeutic antibody an amount sufficient to increase ADCC of a compound, preferably an antibody or a fragment thereof, that blocks the inhibitory receptor of an NK cell. Said therapeutic antibody can be bound by CD16 on NK cells, preferably through its Fc region. Preferably, said therapeutic antibody has a human IgG1 or an IgG3 Fc portion, particularly a monoclonal antibody or a fragment thereof, further preferably a human, humanized or chimeric antibody or a fragment thereof, for instance rituximab.

In an additional aspect, the invention concerns a method of increasing the efficiency of a therapeutic antibody treatment in a subject, said method comprising administering to said subject prior to, simultaneously or after the administration of said therapeutic antibody an amount of a compound, preferably an antibody or a fragment thereof, that blocks the inhibitory receptor of an NK cell, sufficient to increase the efficiency of said therapeutic antibody. Said therapeutic antibody can be bound by CD16, preferably through its Fc region. Preferably, said therapeutic antibody has a human IgG1 or IgG3 Fc portion, particularly a monoclonal antibody or a fragment thereof, further preferably a human, humanized or chimeric antibody or a fragment thereof, for instance rituximab.

Definitions

As used herein, the following terms have the meanings ascribed to them unless specified otherwise.

As used herein, "NK" cells refers to a sub-population of lymphocytes that is involved in non-conventional immunity. NK cells can be identified by virtue of certain characteristics and biological properties, such as the expression of specific surface antigens including CD16, CD56 and/or CD57, the absence of the alpha/beta or gamma/delta TCR complex on the cell surface, the ability to bind to and kill cells that fail to express "self" MHC/HLA antigens by the activation of specific cytolytic enzymes, the ability to kill tumor cells or other diseased cells that express a ligand for NK activating receptors, and the ability to release protein molecules called cytokines that stimulate or inhibit the immune response. Any of these characteristics and activities can be used to identify NK cells, using methods well known in the art.

The term "antibody," as used herein, refers to polyclonal and monoclonal antibodies. Depending on the type of constant domain in the heavy chains, antibodies are assigned to one of five major classes: IgA, IgD, IgE, IgG, and IgM. Several of these are further divided into subclasses or isotypes, such as IgG1, IgG2, IgG3, IgG4, and the like. An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids that is primarily responsible for antigen recognition. The terms variable light chain ($V_L$) and variable heavy chain ($V_H$) refer to these light and heavy chains respectively. The heavy-chain constant domains that correspond to the different classes of immunoglobulins are termed "alpha," "delta," "epsilon," "gamma" and "mu," respectively. The subunit structures and three-dimensional configurations of different classes of immunoglobulins are well known. IgG and/or IgM are the preferred classes of antibodies employed in this invention, with IgG being particularly preferred, because they are the most common antibodies in the physiological situation, because they are most easily made in a laboratory setting, and because IgGs are specifically recognized by Fc gamma receptors. Preferably the antibody of this invention is a monoclonal antibody. Particularly preferred are humanized, chimeric, human, or otherwise-human-suitable antibodies.

Within the context of this invention, the term "therapeutic antibody or antibodies" designates more specifically any antibody that functions to deplete target cells in a patient. In particular, therapeutic antibodies specifically bind to antigens present on the surface of the target cells, e.g., tumor specific antigens present predominantly or exclusively on tumor cells. Preferably, therapeutic antibodies include human Fc portions, or are capable of interacting with human Fc receptors. Therapeutic antibodies can target cells by any means, e.g., ADCC or otherwise, and can be "naked," i.e., with no conjugated moieties, or they can be conjugated with compounds such as radioactive labels or toxins.

The term "specifically binds to" means that an antibody can bind preferably in a competitive binding assay to the binding partner, e.g., an activating NK receptor such as NKp30, NKp44, or NKp46, or a human Fc gamma receptor, as assessed using either recombinant forms of the proteins, epitopes therein, or native proteins present on the surface of isolated NK or relevant target cells. Competitive binding assays and other methods for determining specific binding are further described below and are well known in the art.

A "human-suitable" antibody refers to any antibody, derivatized antibody, or antibody fragment that can be safely used in humans for, e.g., the therapeutic methods described herein. Human-suitable antibodies include all types of humanized, chimeric, or fully human antibodies, or any antibodies in which at least a portion of the antibodies is derived from humans or otherwise modified so as to avoid the immune response that is provoked when native non-human antibodies are used.

By "immunogenic fragment", it is herein meant any polypeptidic or peptidic fragment which is capable of eliciting an immune response such as: (i) the generation of antibodies binding said fragment and/or binding any form of the molecule comprising said fragment, including the membrane-bound receptor and mutants derived therefrom, (ii) the stimulation of a T-cell response involving T-cells reacting to the bi-molecular complex comprising any MHC molecule and a peptide derived from said fragment, (iii) the binding of transfected vehicles such as bacteriophages or bacteria expressing genes encoding mammalian immunoglobulins. Alternatively, an immunogenic fragment also refers to any construction capable to elicit an immune response as defined above, such as a peptidic fragment conjugated to a carrier protein by covalent coupling, a chimeric recombinant polypeptide construct comprising said peptidic fragment in its amino acid sequence, and specifically includes cells transfected with a cDNA of which sequence comprises a portion encoding said fragment.

For the purposes of the present invention, a "humanized" antibody refers to an antibody in which the constant and variable framework region of one or more human immunoglobulins is fused with the binding region, e.g., the CDR, of an animal immunoglobulin. Such humanized antibodies are designed to maintain the binding specificity of the non-human antibody from which the binding regions are derived, but to avoid an immune reaction against the non-human antibody.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. In preferred embodiments of the present invention, the chimeric antibody nevertheless maintains the Fc region of the immunoglobulin, preferably a human Fc region, thereby allowing interactions with human Fc receptors on the surface of target cells.

Within the context of this invention, "potentiated," "active," or "activated" NK cells designate biologically active NK cells, more particularly NK cells having the capacity of lysing target cells. For instance, an "active" NK cell is able to kill cells that express an NK activating receptor-ligand and fails to express "self" MHC/HLA antigens (KIR-incompatible cells). Examples of suitable target cells for use in redirected killing assays are P815 and K562 cells, but any of a number of cell types can be used and are well known in the art (see, e.g., Sivori et al. (1997) J. Exp. Med. 186: 1129-1136; Vitale et al. (1998) J. Exp. Med. 187: 2065-2072; Pessino et al. (1998) J. Exp. Med. 188: 953-960; Neri et al. (2001) Clin. Diag. Lab. Immun. 8:1131-1135). "Potentiated," "active," or "activated" cells can also be identified by any other property or activity known in the art as associated with NK activity, such as cytokine (e.g., IFN-γ and TNF-α) production of increases in free intracellular calcium levels. For the purposes of the present invention, "potentiated," "active," or "activated" NK cells refer particularly to NK cells in vivo that are not inhibited via stimulation of an inhibitory receptor, or in which such inhibition has been overcome, e.g., via stimulation of an activating receptor.

As used herein, the term "activating NK receptor" refers to any molecule on the surface of NK cells that, when stimulated, causes a measurable increase in any property or activity known in the art as associated with NK activity, such as cytokine (for example IFN-γ and TNF-α) production, increases in intracellular free calcium levels, the ability to target cells in a redirected killing assay as described, e.g., elsewhere in the present specification, or the ability to stimulate NK cell proliferation. The term "activating KIR receptor" includes but is not limited to NKp30, NKp44, NKp46, NKG2D, IL-12R, IL-15R, IL-18R and IL-21R. The term "activating NK receptor" as used herein excludes the IL-2 receptor (IL-2R). Methods of determining whether an NK cell is active or proliferating or not are described in more detail below and are well known to those of skill in the art.

As used herein, the term "inhibiting" or "inhibitory" NK receptor" refers to any molecule on the surface of NK cells that, when stimulated, causes a measurable decrease in any property or activity known in the art as associated with NK activity, such as cytokine (e.g., IFN-γ and TNF-α) production, increases in intracellular free calcium levels, or the ability to lyse target cells in a redirected killing assay as described, e.g., elsewhere in the present specification. Examples of such receptors include KIR2DL1, KIR2DL2/3, KIR2DL4, KIR2DL5A, KIR2DL5B, KIR3DL1, KIR3DL2, KIR3DL3, LILRB1, NKG2A, NKG2C NKG2E and LILRB5. Methods of determining whether an NK cell is active or not are described in more detail below and are well known to those of skill in the art.

In the present invention, the term "block an inhibitory receptor or stimulates an activating receptor of an NK cell" refers to the ability of certain compounds, preferably antibodies, fragments or derivatives thereof, to preferably directly interact with at least one inhibitory or activating NK cell receptor, e.g., KIR, NKG2A/C, NKp30, NKp44, NKp46 and others listed herein, and either neutralizing inhibitory signals of the receptor (in the case of inhibitory receptors) or stimulate signalling from the receptor (in the case of activating receptors). With inhibitory receptors, preferably the compound, preferably an antibody or a fragment thereof, is able to block the interaction between HLA and the receptor. When the compound is an antibody, the antibodies may by polyclonal or, preferably, monoclonal. They may be produced by hybridomas or by recombinant cells engineered to express the desired variable and constant domains. The antibodies may be single chain antibodies or other antibody derivatives retaining the antigen specificity and the lower hinge region or a variant thereof such as a Fab fragment, a Fab'2 fragment, a CDR and a ScFv. These may be polyfunctional antibodies, recombinant antibodies, humanized antibodies, or variants thereof.

Within the context of this invention a "common determinant" designates a determinant or epitope that is shared by several members of a group of related receptors, e.g., the human KIR2DL receptor group. The determinant or epitope may represent a peptide fragment or a conformational epitope shared by said members. In a specific embodiment, the common determinant comprises an epitope recognized by monoclonal antibody DF200, NKVSF1 or EB6.

Within the context of this invention, the term antibody that "binds" a common determinant designates an antibody that binds said determinant with specificity and/or affinity, e.g., that essentially does not bind with high affinity or with specificity other unrelated motifs or determinant or structures at the surface of human NK cells. More particularly, the binding of a monoclonal antibody according to this invention to said determinant can be discriminated from the binding of said antibody to another epitope or determinant.

Compounds, preferably antibodies, capable of binding to NK cell inhibitory receptors and prevent their stimulation are thus "neutralizing" or "inhibitory" compounds, preferably antibodies, in the sense that they block, at least partially, the inhibitory signalling pathway mediated by an NK cells inhibitory receptor, i.e., KIR or NKG2A/C receptors. More importantly, this inhibitory activity can be displayed with respect to several types of KIR or NKG2A/C receptors, so that these compounds, preferably antibodies, may be used in various subjects with high efficacy.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under expressed or not expressed at all.

Within the context of the present invention, a subject or patient includes any mammalian subject or patient, more preferably a human subject or patient.

Therapeutic Antibodies

The present invention deals with the use of NK cell potentiating compounds in conjunction with therapeutic antibodies. Any of a large variety of therapeutic antibodies can be used in the present invention. Essentially, any therapeutic antibody, whether "naked" or conjugated with a radiolabel, toxin, or other moiety, or whether full length or a fragment; or whether a true antibody or a modified derivative of an antibody, can be used. Preferably, the methods are used to enhance the efficacy of therapies in which NK cell activity plays a role—not necessarily exclusive—in the efficacy of administered therapeutic antibodies, and also preferably the antibodies or fragments will naturally include, or will be modified to include, a human Fc region or other domain that allows specific recognition of the antibody by human Fc receptors, e.g., Fc gamma receptors.

The present compounds can be used to enhance the ability of therapeutic antibodies to deplete target cells that express an antigen that is specifically recognized by the therapeutic antibodies. Accordingly, any disease or condition that is caused or exacerbated at least in part by cells that can be targeted by a therapeutic antibody can be treated using the herein-described methods. Specific examples of target cells include tumor cells, virus-infected cells, allogenic cells, pathological immunocompetent cells (e.g., B lymphocytes, T lymphocytes, antigen-presenting cells, etc.) involved in allergies, autoimmune diseases, allogenic reactions, etc., or even healthy cells (e.g., endothelial cells in an anti-angiogenic therapeutic strategy). Most preferred target cells within the context of this invention are tumor cells and virus-infected cells. The therapeutic antibodies may, for instance, mediate a cytotoxic effect or cell lysis, particularly by antibody-dependent cell-mediated cytotoxicity (ADCC).

ADCC requires leukocyte receptors for the Fc portion of IgG (FcγR), whose function is to link the IgG-sensitized antigens to FcγR-bearing cytotoxic cells and to trigger the cell activation machinery. Therefore, the therapeutic antibody is capable of forming an immune complex. For example, an immune complex can be a tumor target covered by therapeutic antibodies. More particularly, the antibody can be bound by CD16, preferably through its Fc region. Determining whether a therapeutic antibody binds an Fcγ receptor such as CD16 can be assessed by any suitable manner, for example by determining binding to a recombinant produced CD16 polypeptide or fragment thereof, optionally immobilized on a support, or for example by determining binding of the therapeutic antibody to a cell which known or suspected to express CD16.

The therapeutic antibodies may by polyclonal or, preferably, monoclonal. They may be produced by hybridomas or by recombinant cells engineered to express the desired variable and constant domains. The antibodies may be single chain antibodies or other antibody derivatives retaining the antigen specificity and the lower hinge region or a variant thereof. These may be polyfunctional antibodies, recombinant antibodies, humanized antibodies, fragments or variants thereof. Said fragment or a derivative thereof is preferably selected from a Fab fragment, a Fab'2 fragment, a CDR and a ScFv. Preferably a fragment is an antigen-binding fragment. Therapeutic antibodies which comprise an antibody fragment may also include but are not limited to bispecific antibodies; one example a suitable bispecific antibody comprises an antigen binding region specific for CD16 and an antigen binding region specific for a tumor antigen. Other antibody formats comprising fragments include recombinant bispecific antibody derivatives combining the binding regions of two different antibodies on a single polypeptide chain, also referred to as BiTE™ (Kufer P, et al TRENDS in Biotechnology 2004; 22 (5): 238-244; and Baeuerle et al, Current Opinion in Molecular Therapeutics 2003; 5(4): 413-419, the disclosures of which are incorporated herein by reference.

Therapeutic antibodies are generally specific for surface antigens, e.g., membrane antigens. Most preferred therapeutic antibodies are specific for tumor antigens (e.g., molecules specifically expressed by tumor cells), such as CD20, CD52, ErbB2 (or HER2/Neu), CD33, CD22, CD25, MUC-1, CEA, KDR, αVβ3, etc., particularly lymphoma antigens (e.g., CD20). The therapeutic antibodies have preferably human or non human primate IgG1 or IgG3 Fc portion, more preferably human IgG1.

In one embodiment, the antibodies will include modifications in their Fc portion that enhances the interaction of the antibody with NK cells during ADCC. Such modified therapeutic antibodies ("altered antibodies") generally comprise modifications preferably, in the Fc region that modify the binding affinity of the antibody to one or more FcγR. Methods for modifying antibodies with modified binding to one or more FcγR are known in the art, see, e.g., PCT Publication Nos. WO 2004/016750 (International Application PCT/US2003/025399), WO 99/158572, WO 99/151642, WO 98/123289, WO 89/107142, WO 88/107089, and U.S. Pat. Nos. 5,843,597 and 5,642,821, each of which is incorporated herein by reference in their entirety.

Therapeutic antibodies identified herein, such as D2E7 (Cambridge Antibody Technology Group, plc (Cambridge, UK)/BASF (Ludwigshafen, Germany)) used to treat rheumatoid arthritis, or Infliximab (Centocor, Inc., Malvern, Pa.; used to treat Crohn's disease and rheumatoid arthritis), or the antibodies disclosed in International Patent Application PCT/US2003/025399 (which is hereby incorporated by reference in its entirety) can be modified as taught in the above and below identified applications and used for the treatment of diseases for which such antibodies are typically used. In some embodiments, the invention provides altered antibodies that have altered affinity, either higher or lower affinity, for an activating FcγR, e.g., FcγRIII. In certain preferred embodiments, altered antibodies having higher affinity for FcγR are provided. Preferably such modifications also have an altered Fc-mediated effector function.

Modifications that affect Fc-mediated effector function are well known in the art (See, e.g., U.S. Pat. No. 6,194,351, which is incorporated herein by reference in its entirety). The amino acids that can be modified include but are not limited to proline 329, proline 331, and lysine 322. Proline 329 and/or 331 and lysine 322 can, preferably be replaced with alanine, however, substitution with any other amino acid is also contemplated. See International Publication No.: WO 00/142, 072 and U.S. Pat. No. 6,194,551 which are incorporated herein by reference in their entirety.

Thus, modification of the Fc region can comprise one or more alterations to the amino acids found in the antibody Fc region. Such alterations can result in an antibody with an altered antibody-mediated effector function, an altered binding to other Fc receptors (e.g., Fc activation receptors), an altered ADCC activity, an altered C1q binding activity, an altered complement dependent cytotoxicity activity, or any combination thereof.

In one embodiment, the antibody is specifically recognized by an Fc gamma receptor such as FCGR3A (also called CD16, FCGR3, Immunoglobulin G Fc Receptor III; IGFR3, Receptor for Fc Fragment of IgG, Low Affinity Ixia; see, e.g., OMIM 146740), FCGR2A (also called CD32, CDw32, Receptor for Fc Fragment of IgG, Low Affinity IIa, FCG2, Immunoglobulin G Fc Receptor II; see, e.g., OMIM 146790); FCGR2B (also called CD32, Receptor for Fc Fragment of IgG, Low Affinity IIb; FCGR2B, FC-Gamma-RIIB; see, e.g., OMIM 604590), FCG IRA (also called CD64; Receptor for Fc Fragment of IgG, High affinity Ia; IGFR1; see, e.g., OMIM 146760); FCGR1 fragment of IgG, High affinity Ic, Immunoglobulin G Fc receptor IC, IGFRC; see, e.g., OMIM 601503); or FCGR1B (also called CD64, Receptor for Fc Fragment of IgG, High affinity Ib; Immunoglobulin G Fc Receptor IB,; IGFRB; see, e.g., OMIM 601502).

Typical examples of therapeutic antibodies of this invention are rituximab, alemtuzumab and trastuzumab. Such antibodies may be used according to clinical protocols that have been authorized for use in human subjects. Additional specific examples of therapeutic antibodies include, for instance, epratuzumab, basiliximab, daclizumab, cetuximab, labetuzumab, sevirumab, tuvurimab, palivizumab, infliximab, omalizumab, efalizumab, natalizumab, clenoliximab, etc. Optionally, when a compound that stimulates an activating receptor of an NK cell is a cytokine, the therapeutic antibody is an antibody other than rituximab or herceptin, or optionally other than an anti-CD20 or anti-HER2/neu antibody. Other examples of preferred therapeutic antibodies for use in accordance with the invention include anti-ferritin antibodies (US Patent Publication no. 2002/0106324), anti-p140 and anti-sc5 antibodies (WO 02/50122), and anti-KIR (killer inhibitory receptor) antibodies (The KIR receptors are described in Carrington and Norman, *The KIR Gene Cluster*, May 3, 2003, available at: worldwide web site ncbi.nlm.nih.gov/books), the disclosures of each of the above reference being incorporated herein by reference. Other examples of therapeutic antibodies are listed in the following table, any of which (and others) can be used in the present methods. It will be appreciated that, regardless of whether or not they are listed in the following table or described elsewhere in the present specification, any antibody that can deplete target cells, preferably by ADCC, can benefit from the present methods, and that the following Table 1 is non exhaustive, neither with respect to the antibodies listed therein, nor with respect to the targets or indications of the antibodies that are listed.

TABLE 1

Therapeutic antibodies

| Ab specificity | DCI | Commercial name | Typical Indications |
|---|---|---|---|
| Anti-CD20 | rituximab | MabThera ®, Rituxan ® | NHL B |
| Anti-CD20 | | Zevalin | NHL |
| Anti-CD20 | | Bexocar | NHL |
| Anti-CD52 | alemtuzumab | CAMPATH-1H ® | CLL, allograft |
| Anti-CD33 | | SMART-M195 | AML |
| Anti-CD33 | | Zamyl ™ | Acute myeloid Leukemia |
| Anti-HLA-DR antigen | | SMART-ID10 | NHL |
| Anti-HLA-DR | | Remitogen ™ | NHL B |
| Anti-CD22 | epratuzumab | LymphoCide ™ | NHL B |
| Anti-HER2 | | MDX-210 | Prostate and other cancers |
| Anti-erbB2 (HER-2/neu) | trastuzumab | Herceptin ®, | Metastatic breast cancer |
| Anti-CA125 | | OvaRex | Ovarian cancer |
| Anti-MUC1 | | TriAb | Metastatic breast cancer |
| Anti-MUC1 | | BravaRex | Metastatic cancers |
| Anti-PEM antigen | | Theragyn, Therex | Ovarian cancer, breast cancer |
| Anti-CD44 | bivatuzumab | | Head and neck cancer |
| Anti-gp72 | MAb, idiotypic 105AD7 | | colorectal cancer |
| Anti-EpCAM | Anti-EpCAM; MT201 | IS-IL2 | cancer |
| Anti-VEGF | MAb-VEGF | | metastatic NSCLC, colorectal cancer |
| Anti-CD18 | AMD Fab | | age-related macular degeneration |
| Anti-CD18 | Anti-CD18 | | Myocardial infarction |
| Anti-VEGF receptor | IMC-1cl I | | colorectal cancer |
| anti-nuC242 | nuC242-DM1 | | Colorectal, gastric, and pancreatic cancer |
| Anti-EGFR | MAb425 | | cancer |
| Anti-EGFR | ABX-EGF | | Cancer |
| Anti-EGFR (HER-1, erbB1) | cetuximab | | ENT and colorectal Cancers |
| Anti-MUC-1 | | Therex ® | Breast and epithelial cancers |
| Anti-CEA | | CEAVac | Colorectal cancer |
| Anti-CEA | labetuzumab | CEA-Cide ™ | Solid tumors |
| Anti-αVβ3 | | Vitaxin | Leiomyosarcoma, colorectal and other cancers (anti-angiogenic) |
| Anti-KDR (VEGFR2) | | | Cancers (anti-angiogenic) |
| anti-VRS fusion protein | palivizumab | Synagis ® | Viral diseases |
| Idem | | Numax ™ | Idem |
| CMV | sevirumab | Protovir | CMV Infection |
| HBs | tuvirumab | Ostavir ™ | Hepatitis B |
| Anti-CD25 | basiliximab | Simulect ® | Prevention/treatment allograft rejection |
| Anti-CD25 | daclizumab | Zénapax ® | Prevention/treatment allograft rejection |
| anti-TNF-α | infliximab | Remicade ™ | Crohn's disease, rheumatoid arthritis |
| anti-CD80 | IDEC-114 | | psoriasis |
| anti-IgE | | E-26 | Allergic asthma and rhinitis |
| anti-IgE | omalizumab | Xolair ™ | Asthma |
| anti-IgE | Rhu-mAb E25 | | Allergy/asthma |

TABLE 1-continued

Therapeutic antibodies

| Ab specificity | DCI | Commercial name | Typical Indications |
| --- | --- | --- | --- |
| anti-integrin αL (CD11a, LFA-1) | efalizumab | Xanelim ™ | psoriasis |
| Anti-beta 2 integrin | LDP-01 | | Stroke, allograft rejection |
| anti-integrin αL (CD11a, LFA-1) | anti-CD11a | | psoriasis |
| anti-CD4 | keliximab siplizumab MEDI-507 | | GVHD, psoriasis |
| Anti-CD4 | OKT4A | | Allograft rejection |
| Anti-CD3 | OKT3 | | Allograft rejection |
| Anti-CD3 | SMART-aCD3 | | Autoimmune disease, allograft rejection, psoriasis |
| Anti-CD64 | | | anemia |
| anti-CD147 | | | GvHD |
| anti-integrin α4 (α4β1–α4β7) | natalizumab | Antegren ® | Multiple Sclerosis, Crohn's Disease |
| Anti-integrin β7 | | | Crohn's Disease, ulcerative colitis |
| Alpha 4 beta 7 | LDP-02 | | Ulcerative colitis |
| Anti-HLA-DR10 beta | | Oncolym | NHL |
| Anti-CD3 | | Nuvion | T cell malignancies |
| Anti-GD2 ganglioside | | Trigem | Metastatic melanoma and small cell lung cancer |
| Anti-SK-1 antigen | | | Colorectal and pancreatic carcinoma |
| anti-CD4* | clenoliximab | | |
| anti-IL-8 | ABX-IL8 | | psoriasis |
| Anti-VLA-4 | | Antegren | MS |
| Anti-CD40L | | Antova | SLE, allograft rejection |
| Anti-CD40L | IDEC-131 | | MS, SLE |
| Anti-E-selectin | CDP850 | | psoriasis |
| Anti-CD11/CD18 | Hu23F2G | | MS, stroke |
| Anti-ICAM-3 | ICM3 | | psoriasis |
| Anti-CBL | ABX-CBL | | GVHD |
| Anti-CD147 | | | |
| Anti-CD23 | IDEC-152 | | Asthma, allergies |
| Anti-CD25 | | Simulect | Allograft rejection |
| Anti-T1-ACY | ACY-110 | | Breast cancer |
| Anti-TTS | TTS-CD2 | | Pancreatic, renal cancer |
| Anti-TAG72 | AR54 | | Breast, ovarian, lung cancer |
| Anti-CA19.9 | GivaRex | | Colorectal, pancreatic, gastric |
| Anti-PSA | ProstaRex | | Prostate cancer |
| Anti-HMFG1 | R1550 | | Breast, gastric cancer |
| | pemtumomab | Theragyn | Gastric, ovarian cancer |
| Anti-hCG | CTP-16, CTP-21 | | Multiple cancers |
| Anti collagen Types 1-V | HU177; HUIV26; XL313 | | Multiple cancers |
| Anti-CD46 | | Crucell/J&J | Multiple cancers |
| Anti-17A-1 | Edrecolomab | Panorex | Colorectal cancer |
| Anti-HM1.24 | AHM | | Multiple myeloma |
| Anti-CD38 | Anti-CD38 | | Multiple myeloma |
| Anti-IL15 Receptor | HuMax lymphoma | | Lymphoma |
| Anti-IL6 | B-E8 | | Lymphoma |
| Anti-TRAIL-R1 | TRM-1 | | Multiple cancers |
| Anti-VEGF2 | | | Multiple cancers |
| Anti-BlyS | Lymphostat | | Multiple cancers |
| Anti-SCLC, CEA and DTPA | Pentacea | | Lung cancer |
| Anti-CD52 | CAMPATH | | Leukemia, Lymphoma |
| Anti-Lewis Y antigen | IGN311 | | Epithelial cancers |
| Anti-VE cadherin | E4G10 | | Multiple cancers |
| Anti-CD56 | BB10901, huN901DC1 | | Colorectal, lung cancer |
| Anti-mertansine/mucine | Cantuzumab | | Colorectal, lung, pancreatic cancer |
| Anti-AFP | AFP-cide | | Liver cancer |
| Anti-CSAp | Mu-9 | | Colorectal cancer |
| Anti-CD30 | MDX-060 | | Melanoma, Hodgkins Disease |
| Anti-PSMA | MDX-070 | | Prostate cancer |
| Anti-CD15 | MDX-11 | | Leukemia |

TABLE 1-continued

Therapeutic antibodies

| Ab specificity | DCI | Commercial name | Typical Indications |
|---|---|---|---|
| Anti-TAG72 | MDX-020 | | Colorectal cancer |
| Anti-CD19,CD3 bispecific | MT103 | | Lymphoma |
| Anti-mesothelin antigen | SS1-PE38 | | Brain and ovarian cancer, mesothelioma |
| Anti-DNA and histones | Cotara | | Colorectal, pancreatic, sarcoma, brain and other cancers |
| Anti-a5B1 integrin | Anti-a5 B1 | | Multiple cancers |
| Anti-p97 | SGN17/19 | | Melanoma |
| Anti-CD5 | Genimune | | Leukemia, lymphoma |

Compounds Regulating NK Cell Activity

NK cell activity is regulated by a complex mechanism that involves both stimulating and inhibitory signals. Accordingly, effective NK cell-mediated therapy can be achieved both by a stimulation of these cells or a neutralization of inhibitory signals. It will be appreciated that any compound that has the effect of blocking, inhibiting, or otherwise down-regulating an inhibitory receptor of an NK cell, or of activating, stimulating, or otherwise promoting the activity or expression of an activating receptor of an NK cell, can be used. This includes compounds such as cytokines, as well as small molecules, polypeptides, and antibodies that can bind to NK cell receptors and directly inhibit or stimulate them. It will also be appreciated that the mechanism by which the receptors are blocked or stimulated is not critical to the advantages provided by the invention. For example, the compounds can increase the expression of an activating receptor, or inhibit the expression of an inhibitory receptor, the compounds can prevent the interaction between a ligand and an inhibitory receptor or enhance the interaction between a ligand and an activating receptor, or the compounds can bind directly to the receptors and inhibit them (in the case of inhibitory receptors) or activate them (in the case of activating receptors). The critical parameter is the effect that the compounds have on the ability of therapeutic antibodies to deplete their target cells in vivo.

Any inhibitory receptor on the surface of an NK cell can be targeted by the present compounds. NK cells are negatively regulated by major histocompatibility complex (MHC) class I-specific inhibitory receptors (Kärre et al., 1986; Öhlén et al, 1989; the disclosures of which are incorporated herein by reference). These specific receptors bind to polymorphic determinants of major histocompatibility complex (MHC) class I molecules or HLA and inhibit natural killer (NK) cell lysis. In humans, a family of receptors termed killer Ig-like receptors (KIRs) recognize groups of HLA class I alleles.

There are several groups of KIR receptors, including KIR2DL, KIR2DS, KIR3DL and KIR3DS. KIR receptors having two Ig domains (KIR2D) identify HLA-C allotypes: KIR2DL2 (formerly designated p58.1) or the closely related gene product KIR2DL3 recognizes an epitope shared by group 2 HLA-C allotypes (Cw1, 3, 7, and 8), whereas KIR2DL1 (p58.2) recognizes an epitope shared by the reciprocal group 1 HLA-C allotypes (Cw2, 4, 5, and 6). The recognition by KIR2DL1 is dictated by the presence of a Lys residue at position 80 of HLA-C alleles. KIR2DL2 and KIR2DL3 recognition is dictated by the presence of an Asn residue at position 80. Importantly the great majority of HLA-C alleles have either an Asn or a Lys residue at position 80. One KIR with three Ig domains, KIR3DL1 (p70), recognizes an epitope shared by HLA-Bw4 alleles. Finally, a homodimer of molecules with three Ig domains KIR3DL2 (p140) recognizes HLA-A3 and -A11.

Although KIRs and other class-I inhibitory receptors (Moretta et al, 1997; Valiante et al, 1997; Lanier, 1998; the disclosures of which are incorporated herein by reference) may be co-expressed by NK cells, in any given individual's NK repertoire, there are cells that express a single KIR and thus, the corresponding NK cells are blocked only by cells expressing a specific class I allele group. Accordingly, as described infra, when inhibitory receptors are targeted, the present methods will often involve the administration of compounds that target multiple inhibitory receptors, thereby ensuring a broad-based effect that reaches a maximum range of NK cells.

In certain embodiments, the compound, preferably an antibody or a fragment thereof, blocks an inhibitory receptor of an NK cell, neutralizing the inhibitory signal of at least one inhibitory receptor selected from the group consisting of KIR2DL2, KIR2DL3, KIR2DL1, KIR3DL1, KIR3DL2, NKG2A and NKG2C. More preferably, the compound, preferably an antibody or a fragment thereof, that blocks the inhibitory receptor of an NK cell, is a compound, preferably an antibody or a fragment thereof that neutralizes the inhibitory signal of KIR2DL2, KIR2DL 3 and/or KIR2DL1.

The invention also contemplates the use of a combination of several compounds, preferably antibodies or a fragment thereof, that block different inhibitory receptors of NK cells. Preferably, compounds, preferably antibodies or a fragment thereof, that block inhibitory receptors of NK cells are specific of an inhibitory receptor selected from KIR2DL1, KIR2DL2, KIR2DL3, KIR3DL1, KIR3DL2, NKG2A and NKG2C and are able to inhibit the related KIR- or NKG2A/C-mediated inhibition of NK cell cytotoxicity. For example, the compounds that block inhibitory receptors of NK cells can comprise an antibody having a specificity for KIR2DL1 and an other having a specificity for KIR2DL2 and/or KIR2DL3. More preferably, the combination of compounds that block inhibitory receptors of NK cells is able to inhibit the KIR2DL1-, KIR2DL2-, and KIR2DL3-mediated inhibition of NK cell cytotoxicity. In other embodiments, a cocktail of one or more compounds targeting one or more inhibitory receptors, as well as one or more compounds targeting one or more activating receptors, will be administered.

For example, monoclonal antibodies specific for KIR2DL1 have been shown to block the KIR2DL1 Cw4 (or the like) alleles (Moretta et al., 1993; the disclosure of which is incorporated herein by reference). In an other example, monoclonal antibodies against KIR2DL2/3 have also been described that block the KIR2DL2/3 HLACw3 (or the like)

alleles (Moretta et al., 1993). Anti NKG2A antibodies have been shown to block the inhibitory interaction between NKG2A and HLA-E.

Optionally, the antibody can be selected from the group consisting of GL 183 (KIR2DL2, L3, available from Immunotech, France and Beckton Dickinson, USA); EB6 (KIR2DL1, available from Immunotech, France and Beckton Dickinson, USA); AZI38 (KIR3DL1, available from Moretta et al, Univ. Genova, Italy); Q66 (KIR3DL2, available from Immunotech, France); Z270 (NKG2A, available from Immunotech, France); P25 (NKG2A/C, available from Moretta et al., Univ. Genova, Italy); and DX9, Z27 (KIR3DL1, available from Immunotech, France and Beckton Dickinson, USA).

In a preferred aspect, the invention uses monoclonal antibodies, as well as fragments and derivatives thereof, wherein said antibody, fragment or derivative cross reacts with several KIR or NKG2A/C receptors at the surface of NK cells and neutralizes their inhibitory signals.

In one embodiment, the invention uses a monoclonal antibody that binds a common determinant of human KIR2DL receptors and inhibit the corresponding inhibitory pathway. Preferably, the invention uses a monoclonal antibody that binds KIR2DL1 and KIR2DL2/3 receptors at the surface of human NK cells and inhibits KIR2DL1- and KIR2DL2/3-mediated inhibition of NK cell cytotoxicity. The antibody specifically inhibits binding of HLA-c molecules to KIR2DL1 and KIR2DL2/3 receptors. More preferably, the antibody facilitates NK cell activity in vivo. Because KIR2DL1 and KID2DL3 (or KIR2DL2) are sufficient for covering most of the HLA-C allotypes, respectively group 1 HLA-C allotypes and group 2 HLA-C allotypes, such antibodies may be used to increase the efficiency of a therapeutic antibody in most human individuals, typically in about 90% of human individuals or more. In such an embodiment, any of the antibodies described in PCT Patent Application no. PCT/FR 04/01702 filed Jul. 1, 2004, titled "Compositions and methods for regulating NK cell activity" can be used in accordance with the invention, the disclosure of which is incorporated herein by reference.

In a particular object of this invention, the antibody that blocks the inhibitory receptor of an NK cell is a monoclonal antibody, wherein said antibody binds a common determinant of KIR2DL human receptors and inhibits KIR2DL-mediated inhibition of NK cell cytotoxicity. The antibody more specifically binds to the same epitope as monoclonal antibody DF200 or NKVSF1 produced by hybridoma DF200 and NKVSF1 respectively and/or competes with monoclonal antibody DF200 or NKVSF1 produced by hybridoma DF200 and NKVSF1 respectively, for binding to a KIR receptor at the surface of a human NK cell. As discussed, examples of antibodies, functional assays and assays to determine whether antibodies compete for binding with said antibodies are described in PCT Patent Application no. PCT/FR 04/01702.

In a specific embodiment, the monoclonal antibody is monoclonal antibody DF200 produced by hybridoma DF200. In another embodiment, the monoclonal antibody is EB6, or the antibody binds to the same epitope as monoclonal antibody EB6, or competes for binding with monoclonal antibody EB6. In other embodiments, the antibody is a fragment or derivative of either of antibodies DF200 or EB6. The hybridoma producing antibody DF200 has been deposited at the CNCM culture collection, as Identification no. "DF200", registration no. CNCM 1-3224, registered 10 Jun. 2004, Collection Nationale de Cultures de Microorganismes, Institut Pasteur, 25, Rue du Docteur Roux, F-75724 Paris Cedex 15, France. The antibody NKVSF1 is available from Serotec (Cergy Sainte-Christophe, France), Catalog ref no. MCA2243.

In another embodiment of the present invention, the compound used to enhance the efficacy of therapeutic antibodies stimulates an activating receptor of an NK cell. Any activating receptor can be used, e.g., NKp30 (see, e.g., PCT WO 01/36630, the disclosure of which is herein incorporated by reference in its entirety), NKp44 (see, e.g., Vitale et al. (1998) J. Exp. Med. 187:2065-2072, the disclosure of which is herein incorporated by reference in its entirety), NKp46 (see, e.g., Sivori et al. (1997) J. Exp. Med. 186:1129-1136; Pessino et al. (1998) J. Exp. Med. 188:953-960; the disclosures of which are herein incorporated by reference in their entireties), NKG2D (see, e.g., OMIM 602893), IL-12R, IL-15R, IL-18R, IL-21R, or an activatory KIR receptor, for example a KIR2DS4 receptor (Carrington and Norman, The KIR Gene Cluster, May 3, 2003, available at: worldwide web site ncbi.nlm.nih.gov/books), or any other receptor present on a substantial fraction of NK cells, and whose activation leads to the activation or proliferation of the cell, preferably even if the cell had previously been inhibited via an inhibitory receptor such as an inhibitory KIR receptor. The compound can be any molecular entity, including polypeptides, small molecules, and antibodies. Exemplary compounds include any ligands, including natural, recombinant or synthetic ligands, which interact with activating receptors. For example, a compound which stimulates an activating receptor of an NK cell may be a cytokine such as IL-12 which interacts with the IL-12 receptor (IL-12R), IL-15 which interacts with the IL-15 receptor (IL-15R), IL-18 which interacts with the IL-18 receptor (IL-18R), IL-21 which interacts with the IL-21 receptor (IL-21R). Such compounds are known from e.g., IL-12 (Research Diagnostics, NJ, DI-212), IL-15 (Research Diagnostics, NJ, RDI-215), IL-21 (Asano et al, FEBS Lett. 2002;528:70-6). Preferably, a compound which stimulates an activating receptor of an NK cell is a compound other than IL-2. Other exemplary compounds which stimulate an activating receptor of an NK cell include antibodies which bind an NK cell receptor selected from the group consisting of NKp30, NKp44, NKp46, NKG2D, KIR2DS4 and other activatory KIR receptors.

In certain preferred embodiments, the activatory receptor is a Natural Cytotoxicity Receptor (NCR) found on NK cells, preferably the NCR selected from the group consisting of NKp30, NKp44 or NKp46, and the compound that stimulates an activating receptor is, binds to the same epitope as, or competes for binding with any of the monoclonal antibodies selected from the group consisting of AZ20, A76, Z25, Z231, and BAB281.

The binding of any compound to any of the herein-described NK cell receptors can be detected using any of a variety of standard methods. For example, colorimetric ELISA-type assays can be used, as can immunoprecipitation and radioimmunoassays. Competition assays may be employed, e.g., to compare the binding of a test compound to a compound known to bind to an NK cell receptor, in which the control (e.g., BAB281, which specifically binds to NKp46) and test compounds are admixed (or pre-adsorbed) and applied to a sample containing the epitope-containing protein, e.g., NKp46 in the case of BAB281. Protocols based upon ELISAs, radioimmunoassays, Western blotting and the use of BIACORE are suitable for use in such simple competition studies and are well known in the art.

Inhibition of KIR- or NKG2A/C-mediated inhibition of NK cell cytotoxicity, or stimulation of NKp30, NKp44, NKp46, or NKG2D-mediated activation of NK cells, can be assessed by various assays or tests, such as binding, cytotoxicity, or other molecular or cellular assays.

In a specific variant, inhibitory activity is illustrated by the capacity of said compound, preferably an antibody, to reconstitute the lysis of KIR or NKG2A/C positive NK clones, respectively, on HLA-C or HLA-E positive targets. In another specific embodiment, the compound, preferably an antibody, is defined as inhibiting the binding of HLA-C molecules to KIR2DL1 and KIR2DL3 (or the closely related KIR2DL2) receptors, further preferably as its capacity to alter the binding of a HLA-C molecule selected from Cw1, Cw3, Cw7, and Cw8 (or of a HLA-c molecule having an Asn residue at position 80) to KIR2DL2/3; and the binding of a HLA-C molecule selected from Cw2, Cw4, Cw5 and Cw6 (or of a HLA-c molecule having a Lys residue at position 80) to KIR2DL1.

The inhibitory or potentiating activity of a compound of this invention, preferably an antibody, can be assessed in any of a number of ways, e.g., by its effect on intracellular free calcium as described, e.g., in Sivori et al. (1997) J. Exp. Med. 186:1129-1136, the disclosure of which is herein incorporated by reference. NK cell activity can also be assessed using a cell based cytotoxicity assays, e.g., measuring chromium release, such as assessing the ability of the antibody to stimulate NK cells to kill target cells such as P815, K562 cells, or appropriate tumor cells as disclosed in Sivori et al. (1997) J. Exp. Med. 186: 1129-1136; Vitale et al. (1998) J. Exp. Med. 187: 2065-2072; Pessino et al. (1998) J. Exp. Med. 188: 953-960; Neri et al. (2001) Clin. Diag. Lab. Immun. 8:1131-1135); Pende et al. (1999) J. Exp. Med. 190: 1505-1516), the entire disclosures of each of which are herein incorporated by reference. Suitable cytotoxicity assays are also provided in the examples section of the present specification. In a preferred embodiment, the antibodies cause at least a 10% augmentation in NK cytotoxicity, preferably at least a 40% or 50% augmentation in NK cytotoxicity, or more preferably at least a 70% augmentation in NK cytotoxicity.

NK cell activity can also be addressed using a cytokine-release assay, wherein NK cells are incubated with the antibody to stimulate the NK cells' cytokine production (for example IFN-γ and TNF-α production). In an exemplary protocol, IFN-γ production from PBMC is assessed by cell surface and intracytoplasmic staining and analysis by flow cytometry after 4 days in culture. Briefly, Brefeldin A (Sigma Aldrich) is added at a final concentration of 5 µg/ml for the last 4 hours of culture. The cells are then incubated with anti-CD3 and anti-CD56 mAb prior to permeabilization (IntraPrep™; Beckman Coulter) and staining with PE-anti-IFN-γ or PE-IgG1 (Pharmingen). GM-CSF and IFN-γ production from polyclonal activated NK cells are measured in supernatants using ELISA (GM-CSF: DuoSet Elisa, R&D Systems, Minneapolis, Minn.; IFN-γ: OptE1A set, Pharmingen).

In a preferred embodiment, the ability of the antibody to activate human NK cells is assessed, where an ability to activate human NK cells at least as well as non-human NK cells indicates that the compounds are suitable for use in the present invention. In particular, the ability of the compound to enhance the ability of therapeutic antibodies to direct the depletion of suitable target cells by NK cells in vitro or in vivo can be assessed.

The compounds of this invention, preferably antibodies, may exhibit partial inhibitory or stimulating activity, e.g., partially reduce the KIR2DL-mediated inhibition of NK cell cytotoxicity, or partially activate an NK cell through any level of stimulation of NCRs or other receptors. Most preferred compounds are able to inhibit (or stimulate, in the case of activating receptors) at least 20%, preferably at least 30%, 40% or 50% or more of the activity of the NK cell, e.g., as measured in a cell toxicity assay, in comparison to cells in the absence of the compound. Also preferred, the compound can provide an increase of depletion of target cells by 10%, 20%, 30%, 40%, 50%, 60%, 70%, 80%, 90%, 100%, 200%, 300%, 400%, 500%, 1000%, or more relative to the depletion level in the absence of the compound. Alternatively, preferred compounds of this invention, preferably antibodies, are able to induce the lysis of matched or HLA compatible or autologous target cell population, i.e., cell population that would not be effectively lysed by NK cells in the absence of said antibody. Accordingly, compounds of this invention may also be defined as facilitating NK cell activity in vivo.

The invention also contemplates embodiments in which compounds that stimulate activating receptors, or, preferably, block the inhibitory receptor of an NK cell, are fragments of such a monoclonal antibody having substantially the same antigen specificity, including, without limitation, a Fab fragment, a Fab'2 fragment, a CDR and a ScFv. Furthermore, the monoclonal antibody may be humanized, human, or chimeric (e.g., a bispecific or functionalised antibody). While antibodies stimulating activating receptors can also be fragments, they are preferably full length. Derivatives, e.g., with modified sequences or with conjugated heterologous functional groups or other compounds, can be used for any of the antibodies described herein.

The antibodies that block the inhibitory receptor or stimulate an activating receptor of an NK cell according to the invention may be produced by a variety of techniques known in the art. Typically, they are produced by immunization of a non-human animal with an immunogen comprising a KIR, NKG2A/C, NCR (e.g., NKp30, NKp44, NKp46), or NKG2D polypeptide, or immunogenic fragment of any of the polypeptides, and collection of spleen cells (to produce hybridomas by fusion with appropriate cell lines). Methods of producing monoclonal antibodies from various species are well known in the art (see, e.g., Harlow et al., "Antibodies: A laboratory Manual," CSH Press, 1988; Goding, "Monoclonal Antibodies: Principles and Practice," Academic Press, 1986; the disclosures of which are incorporated herein by reference). More specifically, these methods comprise immunizing a non-human animal with the antigen, followed by a recovery of spleen cells which are then fused with immortalized cells, such as myeloma cells. The resulting hybridomas produce the monoclonal antibodies and can be selected by limiting dilutions to isolate individual clones. Antibodies may also be produced by selection of combinatorial libraries of immunoglobulins, as disclosed for instance in Ward et al. (1989); the disclosure of which is incorporated herein by reference.

Preferred antibodies that block the inhibitory receptor or stimulate an activating receptor of an NK cell according to the invention are prepared by immunization with an immunogen comprising an activating or inhibiting NK cell receptor, e.g., a KIR2DL polypeptide, more preferably a human KIR2DL polypeptide. The KIR2DL polypeptide may comprise the full length sequence of a human KIR2DL polypeptide, or a fragment or derivative thereof, typically an immunogenic fragment, i.e., a portion of the polypeptide comprising an epitope, preferably a T or B cell epitope. Such fragments typically contain at least 7 consecutive amino acids of the mature polypeptide sequence, even more preferably at least 10 consecutive amino acids thereof. They are essentially derived from the extra-cellular domain of the receptor. In a preferred embodiment, the immunogen comprises a wild-type human KIR2DL, NCR, or other polypeptide in a lipid membrane, typically at the surface of a cell. In a specific embodiment, the immunogen comprises intact NK cells, particularly intact human NK cells, optionally treated or lysed.

While the therapeutic antibodies may have Fc regions modified so as to enhance their binding by receptors such as CD16, in certain embodiments NK cell potentiating antibodies will have Fc regions altered so as to reduce their affinity for Fc receptors, thereby reducing the likelihood that NK cells bound by the antibodies will themselves be bound and lysed.

Antibodies that block the KIR2DL receptors of NK cells can be produced by methods comprising: i) immunizing a non-human mammal with an immunogen comprising a KIR2DL polypeptide; ii) preparing monoclonal antibodies from said immunized animal, wherein said monoclonal antibodies bind said KIR2DL polypeptide; iii) selecting monoclonal antibodies from step ii) that cross react with at least two different serotypes of KIR2DL polypeptides; and iv) selecting monoclonal antibodies of (c) that inhibit KIR2DL-mediated inhibition of NK cells.

The order of steps (iii) and (iv) can be changed. Optionally, the method may further comprise additional steps of making fragments or derivatives of the monoclonal antibody, as disclosed below.

In an other variant, the method comprises: i) selecting, from a library or repertoire, a monoclonal antibody or a fragment or derivative thereof that cross reacts with at least two different serotypes of KIR2DL polypeptides; and selecting an antibody from step i) that inhibits KIR2DL-mediated inhibition of NK cells.

It will be appreciated that any of these methods can be used to select for any antibodies or anybody fragments that are specific for any group of (inhibitory or activating) NK cell receptors sharing one or more epitopes. For example, similar methods can be used for the preparation of antibodies that block a KIR3DL or a or NKG2A/C receptor of NK cells, or stimulate an activating receptor of NK cells.

In preferred embodiment, the non-human animals used in these methods, or used in the production of any of the herein-described antibodies, is a mammal, such as a rodent (e.g., mouse, rat, etc.), bovine, porcine, horse, rabbit, goat, sheep, etc.

Also, any of the herein-described antibodies can be genetically modified or engineered to be human-suitable, e.g., humanized, chimeric, or human antibodies. Methods for humanizing antibodies are well known in the art. Generally, a humanized antibody according to the present invention has one or more amino acid residues introduced into it from the original antibody. These murine or other non-human amino acid residues are often referred to as "import" residues, which are typically taken from an "import" variable domain. Humanization can be essentially performed following the method of Winter and co-workers (Jones et al. (1986) Nature 321:522; Riechmann et al. (1988) Nature 332:323; Verhoeyen et al. (1988) Science 239:1534 (1988)). In some cases, such "humanized" antibodies are chimeric antibodies (Cabilly et al., U.S. Pat. No. 4,816,567), wherein substantially less than an intact human variable domain has been substituted by the corresponding sequence from the original antibody. In practice, humanized antibodies according to this invention are typically human antibodies in which some CDR residues and possibly some FR residues are substituted by residues from analogous sites in the original antibody.

Another method of making "humanized" monoclonal antibodies is to use a XenoMouse® (Abgenix, Fremont, Calif.) as the mouse used for immunization. A XenoMouse is a murine host that has had its immunoglobulin genes replaced by functional human immunoglobulin genes. Thus, antibodies produced by this mouse or in hybridomas made from the B cells of this mouse, are already humanized. The XenoMouse is described in U.S. Pat. No. 6,162,963, which is herein incorporated in its entirety by reference. An analogous method can be achieved using a HuMAb-Mouse™ (Medarex).

Human antibodies may also be produced according to various other techniques, such as by using, for immunization, other transgenic animals that have been engineered to express a human antibody repertoire (Jakobovitz et al., Nature 362 (1993) 255), or by selection of ant body repertoires using phage display methods. Such techniques are known to the skilled person and can be implemented starting from monoclonal antibodies as disclosed in the present application.

The antibodies of the present invention may also be derivatized to "chimeric" antibodies (immunoglobulins) in which a portion of the heavy and/or light chain is identical with or homologous to corresponding sequences in the original antibody, while the remainder of the chain(s) is identical with or homologous to corresponding sequences in antibodies derived from another species or belonging to another antibody class or subclass, as well as fragments of such antibodies, so long as they exhibit the desired biological activity (Cabilly et al., supra; Morrison et al. (1984) Proc. Natl. Acad. Sci. 81:6851).

It will also be appreciated that when the compound that blocks the inhibitory receptor of an NK cell or stimulates an activatory receptor of an NK cell is an antibody, such antibody may by polyclonal or, preferably, monoclonal. The antibody may be produced by a hybridoma or by a recombinant cell engineered to express the desired variable and constant domains. The antibody may be a single chain antibody or other antibody derivative retaining the antigen specificity and the lower hinge region or a variant thereof. The antibody may be a polyfunctional antibody, recombinant antibody, humanized antibody, or a fragment or derivative thereof. Said fragment or a derivative thereof is preferably selected from a Fab fragment, a Fab'2 fragment, a CDR and a ScFv. Preferably a fragment is an antigen-binding fragment. An antibody that comprises an antibody fragment may also include but are not limited to bispecific antibodies. One example is a bispecific antibody comprising an antigen binding region specific for an activatory receptor and an antigen binding region specific for a tumor antigen (see PCT Publication no. WO 01/71005, the disclosures of which are incorporated herein by reference).

Composition and Administration

The invention concerns a composition comprising at least one compound, preferably an antibody or a fragment thereof, that blocks the inhibitory receptor or stimulates an activating receptor of an NK cell, and a therapeutic antibody, the use of said composition for increasing the efficiency of the therapeutic antibody, for increasing ADCC in a subject treated with a therapeutic antibody, or for treating a subject having a disease, more particularly a disease requiring the depletion of the targeted cells, preferably diseased cells such as virally-infected cells, tumor cells or other pathogenic cells. Preferably, the disease is selected from the group consisting of a cancer, an auto-immune disease, an inflammatory disease, a viral disease. The disease also concerns a graft rejection, more particularly allograft rejection, and graft versus host disease (GVHD).

More particularly, the treatment of the disease requires the depletion of the targeted cells, preferably the diseased cells such as virally-infected cells, tumor cells or other pathogenic cells. Preferably, the disease is a cancer, infectious or immune disease. More preferably, the disease is selected from the group consisting of a cancer, an auto-immune disease, an inflammatory disease, a viral disease. The disease also concerns a graft rejection, more particularly allograft rejection, and graft versus host disease (GVHD).

Said diseases include neoplastic proliferation of hematopoietic cells. Optionally, said diseases are selected from the group consisting of lymphoblastic leukemia, acute or chronic myelogenous leukemia, Hodgkin's lymphoma, Non-Hodgkin's lymphoma, myelodysplastic syndrome, multiple myeloma, and chronic lymphocytic leukemia. Said diseases also include ENT cancers, colorectal cancers, breast cancer, epithelial cancer. Said diseases include CMV infection, and hepatitis B. Said diseases include Crohn's disease, rheumatoid arthritis, asthma, psoriasis, multiple sclerosis or diabetes. In particular, any disease listed in the table provided supra can be treated.

Said therapeutic antibody can be bound by CD16, preferably through its Fc region. Preferably, said therapeutic antibody has a human IgG1 or an IgG3 Fc portion, particularly a monoclonal antibody or a fragment thereof, further preferably a human, humanized or chimeric antibody or a fragment thereof, for instance rituximab.

Said compound, preferably an antibody or a fragment thereof, that blocks the inhibitory receptor or stimulates an activating receptor of an NK cell binds at least one of KIR, NKG2A/C, NCR, or NKG2D human receptors, and either inhibits the related KIR2DL, KIR3DL and/or NKG2A/C-mediated inhibition of NK cell cytotoxicity, or stimulates the related NCR or NKG2D-mediated activation of NK cell cytotoxicity. In one preferred embodiment, a KIR2DL human receptor is used, e.g., a receptor selected from the group consisting of KIR2DL1, KIR2DL2, KIR2DL3 human receptors, or a KIR3DL human receptor is used, e.g., a receptor selected from the group consisting of KIR3DL1 and KIR3DL2.

In one preferred embodiment, the NK-cell potentiating compound binds at least one of KIR2DL human receptors and inhibits the related KIR2DL-mediated inhibition of NK cell cytotoxicity. Preferably, the KIR2DL human receptor is selected from the group consisting of KIR2DL1, KIR2DL2, KIR2DL3 human receptors. In a preferred embodiment, the compound, preferably an antibody or a fragment thereof, binds a common determinant of KIR2DL human receptors and inhibits KIR2DL-mediated inhibition of NK cell cytotoxicity. More preferably, said compound, preferably an antibody, binds a common determinant of KIR2DL1, KIR2DL2, KIR2DL3 human receptors and inhibits KIR2DL1-, KIR2DL2-, KIR2DL3-mediated inhibition of NK cell cytotoxicity. In a particular embodiment, said compound, preferably an antibody, inhibits the binding of a HLA-C allele molecule having a Lys residue at position 80 to a human KIR2DL1 receptor, and the binding of a HLA-C allele molecule having an Asn residue at position 80 to human KIR2DL2 and KIR2DL3 receptors. In an other particular embodiment, this antibody binds to the same epitope as monoclonal antibody DF200 produced by hybridoma DF200. Optionally, this antibody competes with monoclonal antibody DF200 produced by hybridoma DF200 for binding to a KIR receptor at the surface of a human NK cell. In one preferred embodiment, the antibody is monoclonal antibody DF200 produced by hybridoma DF200. In another embodiment, the antibody is, competes with, or binds to the same epitope as monoclonal antibody EB6.

The composition according to the present invention can comprise a combination of several compounds, preferably antibodies or a fragment thereof, that block different inhibitory receptors of NK cells, and/or stimulate one or more activating receptors of NK cells. Preferably, compounds, preferably antibodies or a fragment thereof, that block inhibitory receptors of NK cells are specific of an inhibitory receptor selected from KIR2DL1, KIR2DL2, KIR2DL3, KIR3DL1, KIR3DL2, NKG2A and NKG2C, and are able to inhibit the related KIR— or NKG2A/C-mediated inhibition of NK cell cytotoxicity. More preferably, the combination of "neutralizing" compounds is able to inhibit the KIR2DL1-, KIR2DL2-, and KIR2DL3-mediated inhibition of NK cell cytotoxicity. By providing a combination of compounds, a maximum number of different inhibitory receptors will be blocked in a maximum number of patients. Also, combinations of compounds that stimulate different activating compounds (or, as with inhibitory receptors, bind to different epitopes within a single receptor), can be used, e.g., compounds that together lead to the activation of any combination of two or more receptors selected from the group consisting of NKp30, NKp44, NKp46, and NKG2D. Also, combinations comprising one or more compounds that block an inhibitory receptor, and one or more compounds that stimulate an activating receptor, can be used. As described below, in a preferred embodiment, a sample of NK cells can be obtained from a patient prior to the application of the present methods, and the responsiveness of the NK cells to different combinations of compounds, e.g., in the presence of target cells and the therapeutic antibody, can be assessed.

Compositions of this invention may comprise any pharmaceutically acceptable carrier or excipient, typically buffer, isotonic solutions, aqueous suspension, optionally supplemented with stabilizing agents, preservatives, etc. Typical formulations include a saline solution and, optionally, a protecting or stabilizing molecule, such as a high molecular weight protein (e.g., human serum albumin).

Kits are also provided comprising any combination of one or more therapeutic antibodies, one or more NK cell potentiating compounds, and, preferably, instructions for their use.

According to the methods and compositions of the present invention, compounds, preferably an antibody or a fragment thereof, that block an inhibitory receptor or stimulate an activating receptor of an NK cell and therapeutic antibodies are administered in an "efficient" or "therapeutically effective" amount.

The efficient amount of therapeutic antibodies administered to the recipient can be between about 0.1 mg/kg and about 20 mg/kg. The efficient amount of antibody depends however of the form of the antibody (whole Ig, or fragments), affinity of the mAb and pharmacokinetics parameter that must be determined for each particular antibodies.

The efficient amount of compounds, preferably an antibody or a fragment thereof that block the inhibitory receptor or stimulate an activating receptor of an NK cell administered to the recipient can be between about 0.1 mg/kg and about 20 mg/kg. The efficient amount of antibody depends however of the form of the antibody (whole Ig, or fragments), affinity of the mAb and pharmacokinetics parameters that must be determined for each particular antibodies.

In an important embodiment of the invention, the use of the present compounds can allow therapeutic efficacy to be achieved with reduced doses of therapeutic antibodies. The use (e.g., dosage, administration regimen) of therapeutic antibodies can be limited by side effects, e.g., in the case of rituximab, fever, headaches, wheezing, drop in blood pressure, and others. Accordingly, while in many patients a standard dose of the therapeutic antibodies will be administered in conjunction with the herein-described NK cell potentiating compounds (i.e., the recommended dose in the absence of any other compounds), thereby enhancing the efficacy of the standard dose in patients needing ever greater therapeutic efficacy, in other patients, e.g., those severely affected by side effects, the administration of the present compounds will allow therapeutic efficacy to be achieved at a reduced dose of therapeutic antibodies, thereby avoiding side effects. In practice, a skilled medical practitioner will be capable of determining the ideal dose and administrative regimen of the therapeutic antibody and the NK cell potentiating compound for a given patient, e.g., the therapeutic strategy that will be most appropriate in view of the particular needs and overall condition of the patient. Numerous references are available to guide in the determination of proper dosages, for both the therapeutic antibodies and the NK cell potentiating compounds, e.g., Remington: The Science and Practice of Pharmacy, by Gennaro (2003), ISBN: 0781750253; Goodman and Gilmans The Pharmacological Basis of Therapeutics, by Hardman, Limbird & Gilman (2001), ISBN: 0071354697; Rawlins E. A., editor, "Bentley's Textbook of Pharmaceutics", London: Bailliere, Tindall and Cox, (1977); and others.

In one embodiment, a medical practitioner can gradually lower the amount of the therapeutic antibody given in conjunction with the administration of any of the present NK cell potentiating compounds; either in terms of dosage or frequency of administration, and monitor the efficacy of the therapeutic antibody; e.g., monitor NK cell activity; monitor the presence of target cells in the patient, monitor various clinical indications, or by any other means, and, in view of the results of the monitoring, adjust the relative concentrations or modes of administration of the therapeutic antibodies and/or NK potentiating compound to optimize therapeutic efficacy and limitation of side effects.

In another set of embodiments, NK cells will be obtained from the patient prior to the administration of the therapeutic antibody and NK cell potentiating compounds (and, if appropriate, during the treatment), and assessed to determine the ideal compound or suite of compounds to be used for maximum efficacy. For example, the identity of the inhibitory or activating receptors present on the NK cells can be determined, and compounds administered that specifically targeted the most prominent receptors. Alternatively, the obtained NK cells can be incubated with the therapeutic antibody and target cells, and the ability of one or more compounds to enhance target cell depletion can be assessed. Whichever one or more compounds is most effective at enhancing depletion in vitro can then be selected for use in the present treatment methods.

Suitable doses of the compounds and/or therapeutic antibodies can also generally be determined in vitro or in animal models, e.g., in vitro by incubating various concentrations of a, therapeutic antibody in the presence of target cells, NK cells (preferably human NK cells), optionally other immune cells, and varying concentrations of one or more NK cell potentiating compounds, and assessing the extent or rate of target cell depletion under the various conditions, using standard assays (e.g., as described in the examples section). Alternatively, varying dosages of the therapeutic antibodies can be given to animal models for diseases treatable with the antibodies (e.g., an animal model for NHL in the case of rituximab), along with varying dosages of the herein-described compounds, and the efficacy of the antibodies (e.g., as determined by any suitable clinical, cellular, or molecular assay or criterion) in treating the animals can be assessed.

The composition according to the present invention may be injected directly to a subject, typically by intra-venous, intra-peritoneal, intra-arterial, intra-muscular or transdermic route. Several monoclonal antibodies have been shown to be efficient in clinical situations, such as Rituxan (Rituximab) or Xolair (Omalizumab), and similar administration regimens (i.e., formulations and/or doses and/or administration protocols) may be used with the composition of this invention.

Furthermore, the compositions of this invention may further comprise or may be used in combination with other active agents or therapeutic programs such as chemotherapy or other immunotherapies, either simultaneously or sequentially.

In certain preferred example, the method of the invention further comprises one or several injections of two or more compounds that block an inhibitory receptor or stimulate an activating receptor of an NK cell. Thus, these two or more compounds can be used in combination. This can serve to cause an even greater augmentation of ADCC and efficacy of therapeutic antibodies, and/or can serve to reduce the dosage of a particular compound that block an inhibitory receptor or stimulate an activating receptor of an NK cell. For example, compounds such as IL-2 are known to be toxic at increased doses. The invention therefore preferably provides a method of treatment of a disease in a subject in need thereof comprising: a) administering to said subject at least two compounds, preferably an antibody or a fragment thereof, that blocks an inhibitory receptor or stimulates an activating receptor of an NK cell; and b) administering to said subject a therapeutic antibody. For example, a preferred regimen is where said two compounds are (i) a first compound selected from the group consisting of an antibody which stimulates an NCR or NKG2D receptor or an activatory KIR receptor, and an antibody which blocks an inhibitory KIR receptor or NKG2A, and (ii) a second compound selected from the group consisting of IL-12, IL-15, IL-18 and IL-21. The invention therefore further provides a method of treatment of a disease in a subject in need thereof comprising: a) administering to said subject a compound according to the invention, preferably an antibody or a fragment thereof, that blocks an inhibitory receptor or stimulates an activating receptor of an NK cell; and b) administering to said subject a therapeutic antibody; and (c) administering to said subject IL-2. IL2 is available from Research Diagnostics, NJ, RDI-202, or Chiron Corp. (Emeryville, Calif.).

The cytokine can be administered according to any suitable administration regimen, and may be administered before, simultaneously and/or after administration of the compound which blocks an inhibitory receptor or stimulates an activating receptor of an NK cell, and before, simultaneously and/or after administration of therapeutic antibody. In a typical example, the cytokine is administered daily for a period of 5-10 days, the cytokine(s) being first injected on the same day as the first injection of the compound which blocks an inhibitory receptor or stimulates an activating receptor of an NK cell. Said method preferably comprises one or two injections/day of cytokine(s) by subcutaneous route.

The dosage of the cytokine will be chosen depending on the condition of the patient to be treated. In preferred examples, a relatively low dose of cytokine can be used. For example, an effective dose of a cytokine such as IL-2 is typically lower than 1 million units/square meters/day of cytokine(s), when the cytokine-containing pharmaceutical composition is used for daily subcutaneous injection. In a preferred example, IL-2 is injected subcutaneously at daily doses below 1 million units/m2 for 5 to 10 days. Further detail of the use of cytokines is described in International Patent publication no. PCT/EP/0314716 and U.S. patent application No. 60/435,344 titled "Pharmaceutical compositions having an effect on the proliferation of NK cells and a method using the same", the disclosures of which are incorporated herein by reference. Cytokines can be administered according to the manufacturer's instructions, and modification to dosage and administration can be made as described herein with respect to therapeutic antibodies.

It will also be appreciated that the therapeutic antibodies and NK cell potentiating compounds can be coadministered, e.g., co-injected, or can be administered simultaneously but in different formulations, or can be independently administered, e.g., the compound is administered hours, days, or weeks before or after the administration of the compound.

Further aspects and advantages of this invention are disclosed in the following experimental section, which should be regarded as illustrative and not limiting the scope of this application.

EXAMPLES

Example 1

Generation of a pan KIR2DL Antibody

Purification of PBLs and Generation of Polyclonal or Clonal NK Cell Lines

PBLs were derived from healthy donors by Ficoll Hypaque gradients and depletion of plastic adherent cells. To obtain enriched NK cells, PBLs were incubated with anti CD3, anti CD4 and anti HLA-DR mAbs (30 nms at 4° C.), followed by goat anti mouse magnetic beads (Dynal) (30 nms at 4° C.) and immunomagnetic selection by methods known in the art (Pende et al., 1999). CD3 minus, CD4 minus DR minus cells are cultivated on irradiated feeder cells and 100 U/ml Interleukin 2 (Proleukin, Chiron Corporation) and 1.5 ng/ml Phytohemagglutinin A (Gibco BRL) to obtain polyclonal NK cell populations. NK cell are cloned by limiting dilution and clones of NK cells are characterized by flow cytometry for expression of cell surface receptors.

The following clones were used in this study:

CP11, CN5 and CN505 are KIR2DL1 positive clones and are stained by EB6 or XA-141 antibodies. CN12 and CP502 are KIR2DL3 positive clones and are stained by GL183 antibody.

Flow Cytometry Analysis

Monoclonal antibodies (mAbs) used were produced in the laboratory JT3A (IgG2a, anti CD3), EB6 and GL183 (IgG1 anti KIR2DL1 and KIR2DL3 respectively), XA-141 IgM anti KIR2DL1 (same specificity as compared to EB6, anti CD4 (HP2.6), anti DR (D1.12, IgG2a). Instead of JT3A, HP2.6, and DR1.12, commercially available mAbs of the same specificities can be used for example from Beckman coulter Inc, Fullerton, Calif. EB6 and GL183 are commercially available in Beckman Coulter Inc, Fullerton, Calif. XA-141 is not commercially available but EB6 can be used for control reconstitution of lysis as described in (Moretta et al., 1993).

Flow Cytometry

Cells were stained with the appropriate antibodies (30 nms at 4° C.) followed by PE or FITC conjugated polyclonal anti mouse antibodies (Southern Biotechnology Associates Inc). Samples were analysed by cytofluorometric analysis on a FACSAN apparatus (Becton Dickinson, Mountain View, Calif.).

Cytotoxicity Experiments

The cytolytic activity of NK clones was assessed by a standard 4 hr 51Cr release assay. In which effector NK cells were tested on Cw3 or Cw4 positive cell lines known for their sensitivity to NK cell lysis. All the targets are used at 5000 cells per well in microtitration plate and the Effector on target ratio is indicated in the figures (usually 4 effectors per target cells). The cytolytic assay is performed with or without supernatant of indicated monoclonal antibodies at a ½ dilution. The procedure is essentially the same as described in (Moretta et al., 1993).

Generation of New mAbs

Monoclonal antibodies (mAbs) have been generated by immunizing 5-week-old Balb C mice with activated polyclonal or monoclonal NK cell lines as described in (Moretta et al., 1990; the disclosure of which is incorporated herein by reference). After different cell fusions, the mAbs were fist selected for their ability to cross react with EB6 and GL183 positive NK cell lines and clones. Positive monoclonal antibodies were further screened for their ability to reconstitute lysis by EB6 positive or GL183 positive NK clones of Cw4 or Cw3 positive targets respectively.

DF200, a Novel Monoclonal Antibody Against a Common Determinant of KIR2DL Human NK Receptors One of the monoclonal antibodies, the DF200 mAb, was found to react with various members of the KIR family, including: KIR2DL1 and KIR2DL2/3. Regarding the staining of NK cells with DF200 mAb, both KIR2DL1+ and KIR2DL2/3+ cells were stained brightly (FIG. 1).

NK clones expressing one or another (or even both) of these HLA class I-specific inhibitory receptors were used as effectors cells against target cells expressing one or more HLA-C alleles. As expected, KIR2DL1+NK clones displayed little if any cytolytic activity against target cells expressing HLA-Cw4 and KIR2DL3+NK clones displayed little or no activity on Cw3 positive targets. However, in the presence of DF200 mAb (used to mask their KIR2DL receptors) NK clones became unable to recognize their HLA-C ligands and displayed strong cytolytic activity on Cw3 or Cw4 targets.

Figure 2:
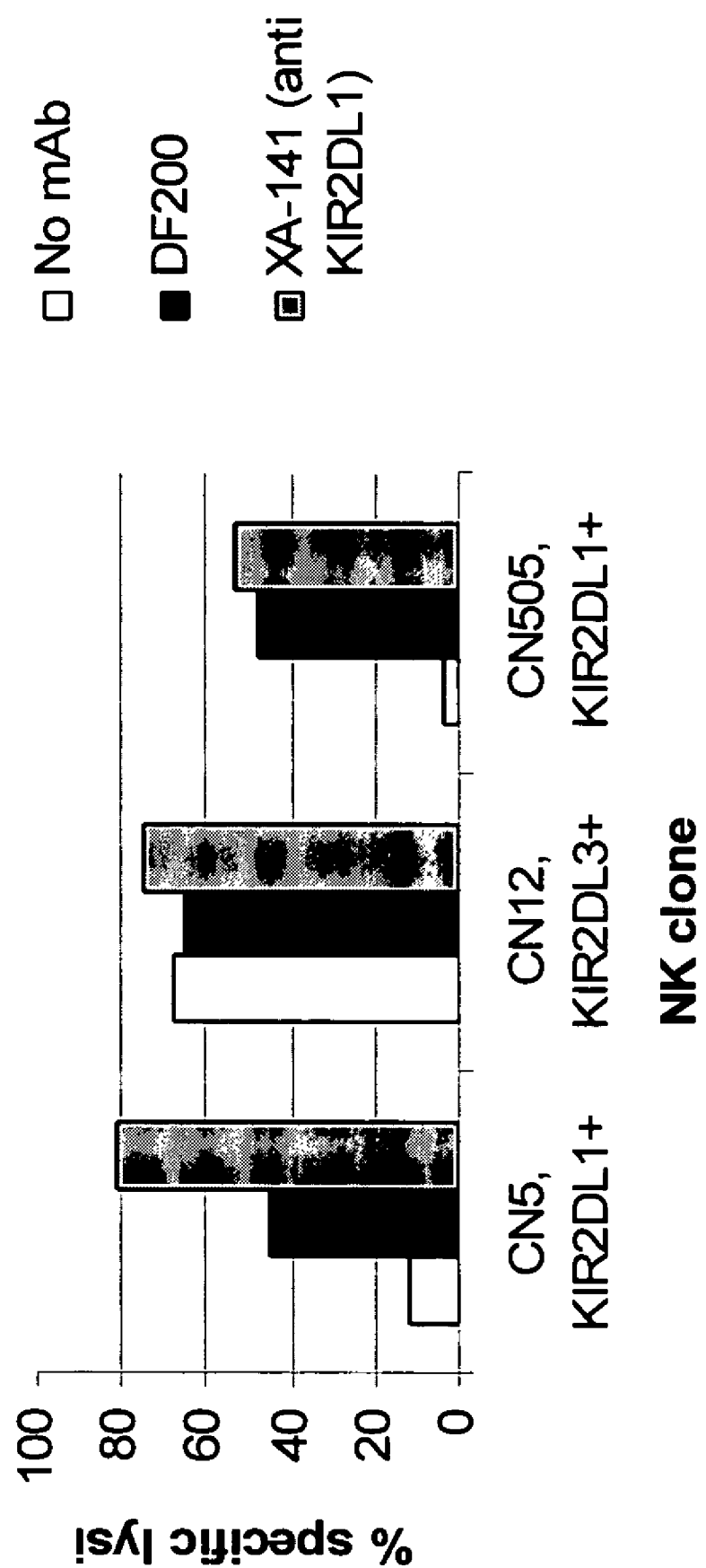
FIG. 2: Reconstitution of lysis with anti-KIR2DL mAb (monoclonal antibody) on CIR Cw4 target at effector/target ratio of 4/1. Monoclonal antibody DF200 inhibits KIR2DL-mediated inhibition of KIR2DL1 positive NK cell cytotoxicity (reconstitute lysis) on Cw4 positive target cells.

For example, the CIR cell line (CW4+EBV cell line, ATCC n°CRL 1993) was not killed by KIR2DL1+NK clones (CN5/CN505), but the inhibition could be efficiently reverted by the use of either DF200 or a conventional anti KIR2DL1 mAb. On the other hand NK clones expressing the KIR2DL2/3+ KIR2DL1-phenotype (CN12) efficiently killed CIR and this killing was unaffected by the DF200 mAb (FIG. 2). Similar results can be obtained with KIR2DL2- or KIR2DL3-positive NK clones on Cw3 positive targets.

Biacore Analysis of DF200 mAb/KIR 2DL1 and DF200 mAb/KIR 2DL3 Interactions

Materials and Methods

Production and purification of recombinant proteins. The KIR 2DL1 and KIR 2DL3 recombinant proteins were produced in *E. coli*. cDNA encoding the entire extracellular domain of KIR 2DL1 and KIR 2DL3 were amplified by PCR from pCDM8 clone 47.11 vector (Biassoni et al, 1993; the disclosure of which is incorporated herein by reference) and RSVS(gpt) 183 clone 6 vector (Wagtman et al, 1995; the disclosure of which is incorporated herein by reference) respectively, using the following primers:

```
                                              (SEQ ID NO:1)
Sense:
5'-GGAATTCCAGGAGGAATTTAAAATGCATGAGGGAGTCCACAG-3'

(SEQ ID NO:2)
Anti-sense:
5'-CCCAAGCTTGGGTTATGTGACAGAAACAAGCAGTGG-3'
```

They were cloned into the pML1 expression vector in frame with a sequence encoding a biotinylation signal (Saulquin et al, 2003; the disclosure of which is incorporated herein by reference).

Protein expression was performed into the BL21(DE3) bacterial strain (Invitrogen). Transfected bacteria were grown to $OD_{600}$=0.6 at 37° C. in medium supplemented with ampicillin (100 µg/ml) and induced with 1 mM IPTG.

Proteins were recovered from inclusion bodies under denaturing conditions (8 M urea). Refolding of the recombinant proteins was performed in Tris 20 mM, pH 7.8, NaCl 150 mM buffer containing L-arginine (400 mM, Sigma) and β-mercaptoethanol (1 mM), at RT, by decreasing the urea concentration in a six step dialysis (4, 3, 2, 1 0.5 and 0 M urea, respectively). Reduced and oxidized glutathion (5 mM and 0.5 mM respectively, Sigma) were added during the 0.5 and 0 M urea dialysis steps. Finally, the proteins were dialyzed extensively against Tris 10 mM, pH 7.5, NaCl 150 mM buffer. Soluble refolded proteins were concentrated and then purified on a Superdex 200 size-exclusion column (Pharmacia; AKTA system).

Biacore analysis. Surface plasmon resonance measurements were performed on a Biacore apparatus (Biacore). In all Biacore experiments HBS buffer supplemented with 0.05% surfactant P20 served as running buffer.

Protein immobilization. Recombinant KIR 2DL1 and KIR 2DL3 proteins were immobilized covalently to carboxyl groups in the dextran layer on a Sensor Chip CM5 (Biacore). The sensor chip surface was activated with EDCINHS(N-ethyl-N'-(3-dimethylaminopropyl)carbodiimidehydrochloride and N-hydroxysuccinimide, Biacore). Proteins, in coupling buffer (10 mM acetate pH 4.5) were injected. Deactivation of the remaining activated groups was performed using 100 mM ethanolamine pH8 (Biacore).

Affinity measurements. For kinetic measurements, various concentrations of the soluble antibody ($10^{-7}$ to $4\times10^{-10}$ M) were applied onto the immobilized sample. Measurements were performed at 20 µl/min continuous flow rate. For each cycle, the surface of the sensor chip was regenerated by 5 µl injection of 10 mM NaOH pH 11.

The BIAlogue Kinetics Evaluation program (BIAevaluation 3.1, Biacore) was used for data analysis.

Results

BIAcore analysis of DF200 mAb binding to immobilized KIR 2DL1 and KIR 2DL3.

|  | $KD (10^{-9} M)$ |
| --- | --- |
| KIR 2DL1 | 10.9 +/– 3.8 |
| KIR 2DL3 | 2.0 +/– 1.9 |

KD: Dissociation constant.

The soluble analyte (40 µl at various concentrations) was injected at a flow rate of 20 µl/min in HBS buffer, on a dextran layers containing 500 or 540 reflectance units (RU), and 1000 or 700 RU of KIR 2DL1 and KIR 2DL3 respectively. Data are representative of 6 independent experiments.

Example 2

Enhancement of ADCC by Using a Combination of Rituxan and Anti KIR mAb

Preparation of human NK clones. Blood mononuclear cells depleted of T cells by negative anti-CD3 immuno-magnetic selection (Miltenyi) are plated under limiting-dilution conditions, activated with phytohemagglutinin (PHA) (Biochrom KG, Berlin, Germany), and cultured with interleukin (IL)-2 (Chiron B.V., Amsterdam, Netherlands) and irradiated feeder cells. Cloning efficiencies are equivalent in all donors and range between 1 in 5 and 1 in 10 plated NK cells. Cloned NK cells are screened for alloreactivity by standard $^{51}$Cr release cytotoxicity against Epstein-Barr virus-transformed B lymphoblastoid cell lines of known HLA type at an effector to target ratio of 10:1. Clones exhibiting ≧30% lysis were scored as alloreactive. As a rule, clones either exhibit <5% or >40% lysis.

Enhancement of ADCC Mediated by Rituxan by a KIR2DL1 Positive NK Cell Clone

Figure 3:
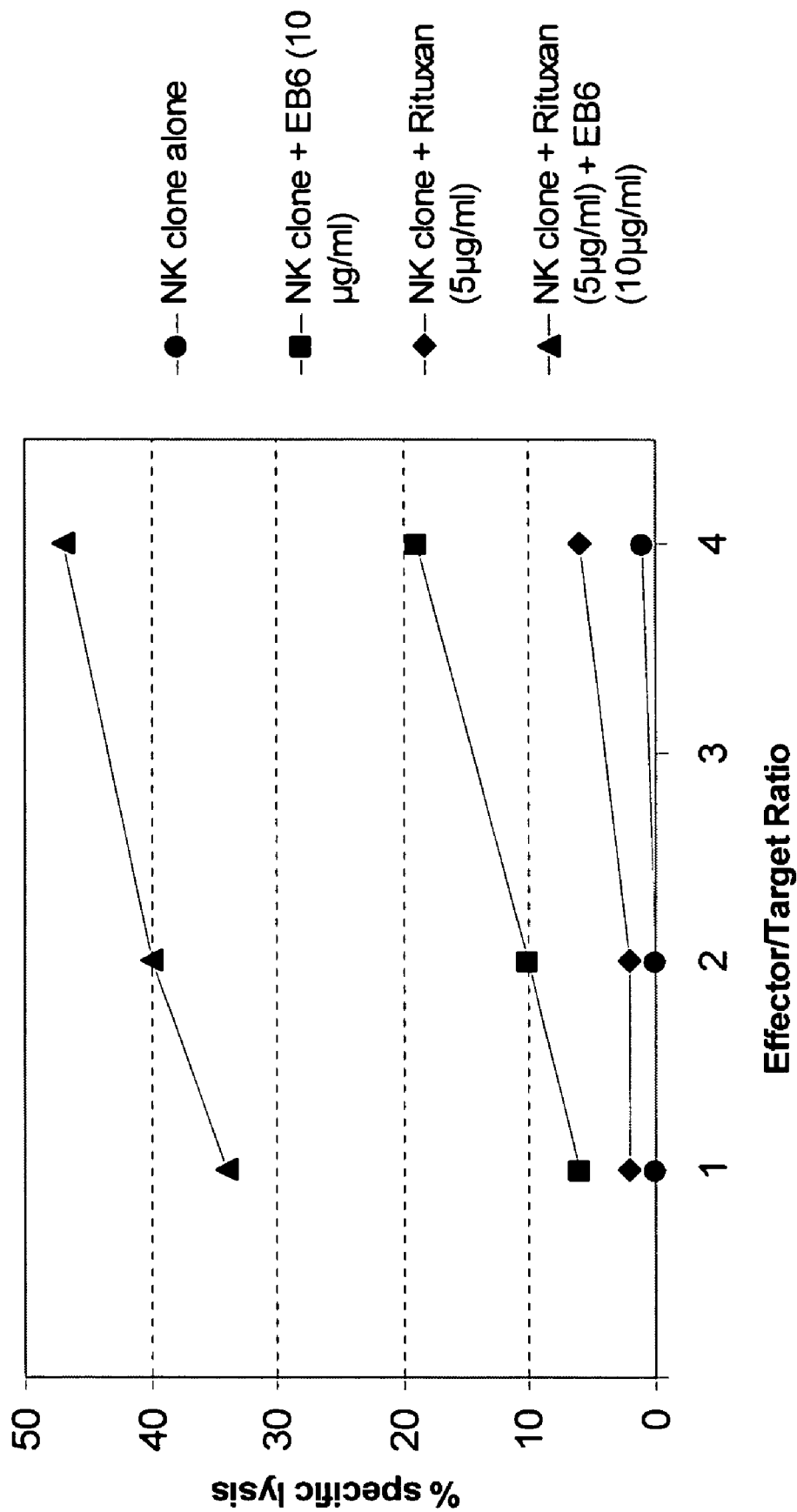
FIG. 3: Enhancement of ADCC mediated by Rituxan of a KIR2DL1 positive NK clone on a Cw4 positive EBV cell line by blocking KIR/HLA interaction. NK clone cytolysis bearing KIR2DL1 is tested against a Cw4 positive EBV transformed (CD20 positive) target cell line at various effector/target ratio (from 1 to 4) in the presence of 5 µg/ml anti CD20 antibody (Rutixan) and 10 µg/ml EB6 antibody (anti KIR2DL1); Rituxan alone; EB6 alone; or without any antibody. ADCC is greatly enhanced in the presence of anti KIR2DL1 antibody (EB6).

The cytolytic activity of NK clone is assessed by a standard 4 hr 51Cr release assay, in which effector NK cells were tested on Cw4 or Cw3 positive EBV cell lines (CD20 positive), known for their sensitivity to NK cell lysis. All the targets are used at 5000 cells per well in microtitration plate and the Effector (NK cell clone) on target ratio is indicated in FIG. 3. In certain experiments, the therapeutic chimeric anti CD20 rituximab (Rituxan, Idec) is added at 5 µg/ml is added to the effector target mixture. In certain experiments, the EB6 antibody (anti KIR2DL1) at 10 µg/ml is added to the effector target mixture.

This experiment showed that Rituxan alone mediates essentially no ADCC by the KIR2DL1 positive NK clone on Cw4 positive target. ADCC of KIR2DL1 positive clone is greatly enhanced in the presence of anti KIR2DL 1 antibody.

Example 3

Enhancement of ADCC Mediated by Campath by a KIR2DL1 Positive NK Cell Clone

Figure 4:
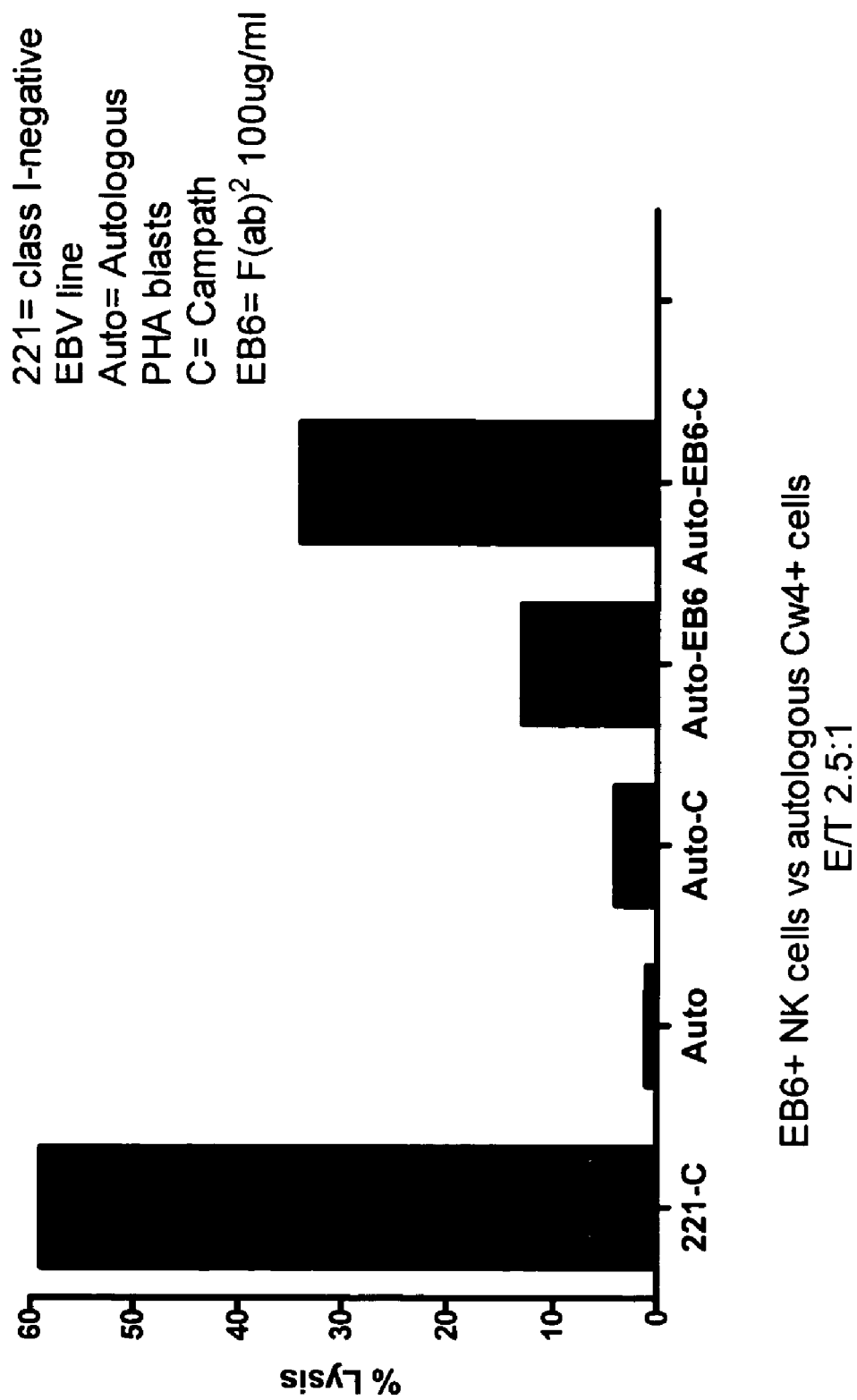
FIG. 4: Enhancement of ADCC mediated by Campath of a KIR2DL1 positive NK clone on a Cw4 positive EBV cell line by blocking KIR/HLA interaction. NK clone cytolysis bearing KIR2DL1 is tested against a Cw4 positive EBV transformed (CD20 positive) target cell line in the presence of Campath and 100 µg/ml EB6 antibody (anti KIR2DL1); Campath alone; EB6 alone; or without any antibody. ADCC is greatly enhanced in the presence of the anti KIR2DL1 antibody (EB6).

In a similar experiment to that described in Example 2, autologous Cw4+PHA blasts were incubated in the presence of NK cells plus alumtuzumab (Campath, Berlex), the EB6 antibody (at 100 ug/ml), or Campath and EB6. The results, shown in FIG. 4, show that the presence of EB6 dramatically enhances the ability of the NK cells to deplete the autologous cells: approximately 4% of the target cells were lysed in the presence of Campath alone, whereas more than 30% of the cells were lysed in the presence of Campath plus EB6.

REFERENCES

Biassoni R, Verdiani S, Cambiaggi A, Romeo P H, Ferrini S, Moretta L. Human CD3-CD16+ natural killer cells express the hGATA-3 T cell transcription factor and an unrearranged 2.3-kb TcR delta transcript. Eur J. Immunol. 1993 May; 23(5):1083-7.

Karre K, Ljunggren H G, Piontek G, Kiessling R, (1986) "Selective rejection of H-2-deficient lymphoma variants suggests alternative immune defence strategy" Nature 319:675-8

Lanier L L (1998)<<NK cell receptors" Annu Rev Immunol 16:359-93

Moretta, A., Bottino, C., Pende, D., Tripodi, G., Tambussi, G., Viale, O., Orengo, A., Barbaresi, M., Merli, A., Ciccone, E., et al. (1990). Identification of four subsets of human CD3-CD16+ natural killer (NK) cells by the expression of clonally distributed functional surface molecules: correlation between subset assignment of NK clones and ability to mediate specific alloantigen recognition. J Exp Med 172, 1589-1598.

Moretta, A., Vitale, M., Bottino, C., Orengo, A. M., Morelli, L., Augugliaro, R., Barbaresi, M., Ciccone, E., and Moretta, L. (1993). P58 molecules as putative receptors for major histocompatibility complex (MHC) class I molecules in human natural killer (NK) cells. Anti-p58 antibodies reconstitute lysis of MHC class I-protected cells in NK clones displaying different specificities. J Exp Med 178, 597-604.

Moretta A, Moretta L (1997) "HLA class I specific inhibitory receptors" Curr Opin Immunol 9:694-701.

Ohlen C, Kling G, Hoglund P, Hansson M, Scangos G, Bieberich C, Jay G, Karre K (1989)" Prevention of allogeneic bone marrow graft rejection by H-2 transgene in donor mice" Science 246:666-8

Pende, D., Parolini, S., Pessino, A., Sivori, S., Augugliaro, R., Morelli, L., Marcenaro, E., Accame, L., Malaspina, A., Biassoni, R., et al. (1999). Identification and molecular characterization of NKp30, a novel triggering receptor involved in natural cytotoxicity mediated by human natural killer cells. J Exp Med 190, 1505-1516.

Ruggeri, L., Capanni, M., Urbani, E., Perruccio, K., Shlomchik, W. D., Tosti, A., Posati, S., Rogaia, D., Frassoni, F., Aversa, F., et al. (2002). Effectiveness of donor natural killer cell alloreactivity in mismatched hematopoietic transplants. Science 295, 2097-2100.

Saulquin X, Gastinel L N, Vivier E. Crystal structure of the human natural killer cell activating receptor KIR2DS2 (CD158j) J Exp Med. 2003 Apr. 7; 197(7):933-8.

Valiante N M, Lienert K, Shilling H G, Smits B J, Parham P (1997)<<Killer cell receptors: keeping pace with MHC class I evolution" Immunol Rev 155:155-64

Wagtmann N, Biassoni R, Cantoni C, Verdiani S, Malnati M S, Vitale M, Bottino C, Moretta L, Moretta A, Long E O. Molecular clones of the p58 NK cell receptor reveal immunoglobulin-related molecules with diversity in both the extra- and intracellular domains. Immunity. 1995 May; 2(5):439-49.

Ward et al. (Nature 341 (1989) 544.

All publications and patent applications cited in this specification are herein incorporated by reference in their entireties as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

Any combination of the above-described elements in all possible variations thereof is encompassed by the invention unless otherwise indicated herein or otherwise clearly contradicted by context.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

The invention claimed is:

1. A method of inhibiting the activity of an inhibitory receptor expressed on a NK cell comprising:
   (a) administering to a subject an antibody or an antigen binding fragment thereof that binds to and inhibits the activity of the KIR2DL1, KIR2DL2/3, KIR2DL4, KIR2DL5A, KIR2DL5B, KIR3DL1, KIR3DL2, KIR3DL3, LILRB1, NKG2A, NKG2C, NKG2E or LILRB5 receptor on a NK cell; and,
   (b) administering to said subject a therapeutic antibody that binds CD16 via the Fc portion of said therapeutic antibody.

2. The method of claim 1, wherein said therapeutic antibody has a human IgG1 or an IgG3 Fc portion.

3. The method of claim 1, wherein said receptor is the KIR2DL1 receptor.

4. The method of claim 1, wherein said therapeutic antibody is a monoclonal antibody.

5. The method of claim 1, wherein said therapeutic antibody is not conjugated with a radioactive or toxic moiety.

6. The method of claim 1, wherein said antibody is a human, humanized or chimeric antibody.

7. The method of claim 4, wherein said therapeutic antibody is a human, humanized or chimeric antibody.

8. The method of claim 7, wherein said therapeutic antibody is rituximab or alemtuzumab (CAMPATH).

9. The method of claim 8, wherein said antibody is rituximab, and said antibody is administered at a dosage of less than 375 mg/m² per week.

10. The method of claim 8, wherein said antibody is alemtuzumab, and said antibody is administered at a dosage of less than 90 mg per week.

11. The method of claim 1, wherein said antibody inhibits the activity of the NKG2A receptor.

12. The method of claim 1, wherein said antibody inhibits an inhibitory receptor of an NK cell selected from the group consisting of KIR2DL1, KIR2DL2/3, KIR2DL4, KIR2DL5A, KIR2DL5B, KIR3DL1, KIR3DL2 and KIR3DL3.

13. The method of claim 3, wherein said antibody binds a common determinant of KIR2DL human receptors and inhibits KIR2DL-mediated inhibition of NK cell cytotoxicity.

14. The method of claim 13, wherein said antibody binds a common determinant of KIR2DL1, KIR2DL2, and KIR2DL3 human receptors and inhibits KIR2DL1-, KIR2DL2-, and KIR2DL3-mediated inhibition of NK cell cytotoxicity.

15. The method of claim 14, wherein said antibody inhibits the binding of a HLA-C allele molecule having a Lys residue at position 80 to a human KIR2DL1 receptor, and the binding of a HLA-C allele molecule having an Asn residue at position 80 to human KIR2DL2 and KIR2DL3 receptors.

16. The method of claim 1, wherein said antibody binds to the same epitope as monoclonal antibody DF200 produced by hybridoma DF200 (deposited as CNCM I-3224), or monoclonal antibody EB6.

17. The method of claim 1, wherein said antibody competes with monoclonal antibody DF200 produced by hybridoma DF200 (deposited as CNCM I-3224), or monoclonal antibody EB6, for binding to a KIR receptor at the surface of a human NK cell.

18. The method of claim 1, wherein said antibody is the monoclonal antibody DF200 produced by hybridoma DF200 (deposited as CNCM I-3224) or an antigen binding fragment thereof or monoclonal antibody EB6 or an antigen binding fragment thereof.

19. The method of claim 1, wherein said therapeutic antibody and said antibody are administered into said subject simultaneously.

20. The method of claim 1, wherein said antibody is administered to said subject within one week of the administration of said therapeutic antibody.

21. The method of claim 1, further comprising an additional step in which the activity or number of NK cells in said patient is assessed prior or subsequent to the administration of said antibody.

22. The method of claim 21, wherein said additional step involves:
   i) obtaining NK cells from said subject prior to said administration;
   ii) incubating said NK cells in the presence of one or more target cells that are recognized by said therapeutic antibody, in the presence or absence of said antibody; and
   iii) assessing the effect of said antibody on the ability of said NK cells to deplete said target cells;
   wherein a detection that said antibody enhances the ability of said NK cells to deplete said target cells indicates that said antibody is suitable for use in said method and said method is suitable for use with said subject.

23. A method of increasing the efficiency of a treatment involving the administration of a therapeutic antibody that can be bound by CD16 in a subject, said method comprising the administration, to a subject, of a therapeutic antibody that can be bound by CD16 via the Fc portion of said therapeutic antibody and administering to said subject prior to, simultaneously with, or following the administration of said therapeutic antibody, a therapeutically-effective amount of an antibody that binds to and blocks an inhibitory receptor of an NK cell.

24. The method of claim 23, wherein said antibody increases the efficiency of said treatment by enhancing ADCC in said subject.

* * * * *

UNITED STATES PATENT AND TRADEMARK OFFICE
CERTIFICATE OF CORRECTION

PATENT NO. : 7,803,376 B2
APPLICATION NO. : 10/897624
DATED : September 28, 2010
INVENTOR(S) : Velardi et al.

It is certified that error appears in the above-identified patent and that said Letters Patent is hereby corrected as shown below:

Column 12,
Lines 34-35, "WO 00/142,072" should read --WO 00/142072--.

Column 12,
Line 54, "FCG IRA" should read --FCG1RA--.

Column 26,
Lines 43-44, "depends however of the form" should read
    --depends however on the form--.
Lines 51-52, "depends however of the form" should read
    --depends however on the form--.

Column 29,
Line 26, "(30 nms at 4° C.)," should read --(30 mns at 4° C.)--.
Line 27, "(30 nms at 4° C.)" should read --(30 mns at 4° C.)--.
Line 33, "NK cell are" should read --NK cells are--.
Line 54, "(30 nms" should read --(30 mns--.

Column 30,
Line 9, "were fist" should read --were first--.
Line 34, "CIR" should read --C1R--.
Line 39, "CIR" should read --C1R--.

Column 31,
Lines 25-26,
    "EDCINHS(N-ethyl-N'-(3-dimethylaminopropyl)carbodiimidehydrochloride"
should read
    --EDC/NHS (N-ethyl-N'-(3-dimethylaminopropyl)carbodiimidehydrochloride--.

Signed and Sealed this
Fifteenth Day of March, 2011

David J. Kappos
*Director of the United States Patent and Trademark Office*

CERTIFICATE OF CORRECTION (continued)
U.S. Pat. No. 7,803,376 B2

Column 32,
Line 34, "alumtuzumab" should read --alemtuzumab--.

Column 33,
Line 26, "<<Killer cell" should read --"Killer cell--.
Line 27, ":155-64" should read --:155-64.--.
Line 35, "(Nature 341 (1989) 544." should read --Nature 341 (1989) 544.--.